US010909679B2

(12) United States Patent
Westerhoff et al.

(10) Patent No.: US 10,909,679 B2
(45) Date of Patent: Feb. 2, 2021

(54) METHOD AND SYSTEM FOR RULE BASED DISPLAY OF SETS OF IMAGES USING IMAGE CONTENT DERIVED PARAMETERS

(71) Applicant: PME IP PTY LTD, Richmond (AU)

(72) Inventors: Malte Westerhoff, Berlin (DE); Detlev Stalling, Berlin (DE)

(73) Assignee: PME IP PTY LTD, Richmond (AU)

( * ) Notice: Subject to any disclaimer, the term of this patent is extended or adjusted under 35 U.S.C. 154(b) by 165 days.

(21) Appl. No.: 16/052,563

(22) Filed: Aug. 1, 2018

(65) Prior Publication Data

US 2019/0096062 A1 Mar. 28, 2019

Related U.S. Application Data

(60) Provisional application No. 62/712,912, filed on Jul. 31, 2018, provisional application No. 62/576,587, (Continued)

(51) Int. Cl.
*G06T 7/00* (2017.01)
*A61B 6/00* (2006.01)
(Continued)

(52) U.S. Cl.
CPC ............ *G06T 7/0014* (2013.01); *A61B 6/463* (2013.01); *A61B 6/466* (2013.01); *A61B 6/5217* (2013.01);
(Continued)

(58) Field of Classification Search
CPC . G06T 2207/30004; G06T 2207/30016; G06T 2207/30032; G06T 2207/30092;
(Continued)

(56) References Cited

U.S. PATENT DOCUMENTS 2,658,310 A 11/1953 Cook
3,431,200 A 3/1969 Davis
(Continued)

FOREIGN PATENT DOCUMENTS

DE 10317384 4/2004
EP 0492897 7/1992
(Continued)

OTHER PUBLICATIONS

Boone et al., Recognition of Chest Radiograph Orientation for Picture Archiving and Communications Systems Display Using Neural Networks, J. Digital Imaging, 1992, 5(3), 190-193.
(Continued)

*Primary Examiner* — Duy M Dang
(74) *Attorney, Agent, or Firm* — Sci-Law Strategies, PC

(57) ABSTRACT

The invention provides, in some aspects, a system for implementing a rule derived basis to display image sets. In various embodiments of the invention, the selection of the images to be displayed, the layout of the images, as well as the rendering parameters and styles can be determined using a rule derived basis. The rules are based on meta data of the examination as well as image content that is being analyzed by neuronal networks. In an embodiment of the present invention, the user is presented with images displayed based on their preferences without having to first manually adjust parameters.

20 Claims, 8 Drawing Sheets

Related U.S. Application Data filed on Oct. 24, 2017, provisional application No. 62/562,460, filed on Sep. 24, 2017.

(51) Int. Cl.
*G16H 30/20* (2018.01)
*G06T 15/08* (2011.01)
*G16H 50/20* (2018.01)

(52) U.S. Cl.
CPC ............ *A61B 6/5294* (2013.01); *G06T 15/08* (2013.01); *G16H 30/20* (2018.01); *G06T 2207/10081* (2013.01); *G06T 2207/10088* (2013.01); *G06T 2207/10104* (2013.01); *G06T 2207/10121* (2013.01); *G06T 2207/10124* (2013.01); *G06T 2207/20081* (2013.01); *G06T 2207/20084* (2013.01); *G06T 2207/30004* (2013.01); *G16H 50/20* (2018.01)

(58) Field of Classification Search
CPC . G06T 2207/30096; G06T 2207/30101; G06T 2207/10072; G06T 2207/10081; G06T 2207/20; G06T 2207/20004; G06T 2207/20021; G06T 2207/20012; G06T 2207/20081; G06T 2207/20084; G06T 7/0012; G06N 20/00; G06N 3/084
See application file for complete search history.

(56) References Cited

U.S. PATENT DOCUMENTS

| | | | |
|---|---|---|---|
| 3,645,040 A | 2/1972 | Ort |
| 4,137,868 A | 2/1979 | Pryor |
| 4,235,043 A | 11/1980 | Harasawa et al. |
| 4,258,661 A | 3/1981 | Margen |
| 4,267,038 A | 5/1981 | Thompson |
| 4,320,594 A | 3/1982 | Raymond |
| 4,746,795 A | 5/1988 | Stewart et al. |
| 4,905,148 A | 2/1990 | Crawford |
| 4,910,912 A | 3/1990 | Lowrey, III |
| 4,928,250 A | 5/1990 | Greenberg et al. |
| 4,958,460 A | 9/1990 | Nielson et al. |
| 4,984,160 A | 1/1991 | Saint Felix et al. |
| 5,031,117 A | 7/1991 | Minor et al. |
| 5,091,960 A | 2/1992 | Butler |
| 5,121,708 A | 6/1992 | Nuttle |
| 5,128,864 A | 7/1992 | Waggener et al. |
| 5,218,534 A | 6/1993 | Trousset et al. |
| 5,235,510 A | 8/1993 | Yamada |
| 5,241,471 A | 8/1993 | Trousset et al. |
| 5,253,171 A | 10/1993 | Hsiao et al. |
| 5,274,759 A | 12/1993 | Yoshioka |
| 5,280,428 A | 1/1994 | Wu et al. |
| 5,287,274 A | 2/1994 | Saint Felix et al. |
| 5,293,313 A | 3/1994 | Cecil |
| 5,307,264 A | 4/1994 | Waggener et al. |
| 5,355,453 A | 10/1994 | Row et al. |
| 5,368,033 A | 11/1994 | Moshfeghi |
| 5,375,156 A | 12/1994 | Kuo-Petravic et al. |
| 5,412,703 A | 5/1995 | Goodenough et al. |
| 5,412,764 A | 5/1995 | Tanaka |
| 5,442,672 A | 8/1995 | Bjorkholm et al. |
| 5,452,416 A | 9/1995 | Hilton |
| 5,488,700 A | 1/1996 | Glassner |
| 5,560,360 A | 10/1996 | Filler |
| 5,594,842 A | 1/1997 | Kaufman et al. |
| 5,602,892 A | 2/1997 | Llacer |
| 5,633,951 A | 5/1997 | Moshfeghi |
| 5,633,999 A | 5/1997 | Clowes et al. |
| 5,640,436 A | 6/1997 | Kawai et al. |
| 5,671,265 A | 9/1997 | Andress |
| 5,744,802 A | 4/1998 | Muehllehner et al. |
| 5,774,519 A | 6/1998 | Lindstrom et al. |
| 5,790,787 A | 8/1998 | Scott et al. |
| 5,793,374 A | 8/1998 | Guenter et al. |
| 5,793,879 A | 8/1998 | Benn et al. |
| 5,813,988 A | 9/1998 | Alfano et al. |
| 5,821,541 A | 10/1998 | Turner |
| 5,825,842 A | 10/1998 | Taguchi |
| 5,838,756 A | 11/1998 | Taguchi et al. |
| 5,841,140 A | 11/1998 | McCroskey et al. |
| 5,909,476 A | 6/1999 | Cheng et al. |
| 5,930,384 A | 7/1999 | Guillemaud et al. |
| 5,931,789 A | 8/1999 | Alfano et al. |
| 5,950,203 A | 9/1999 | Stakuis |
| 5,960,056 A | 9/1999 | Lai |
| 5,963,612 A | 10/1999 | Navab |
| 5,963,613 A | 10/1999 | Navab |
| 5,963,658 A | 10/1999 | Klibanov et al. |
| 6,002,739 A | 12/1999 | Heumann |
| 6,018,562 A | 1/2000 | Willson |
| 6,032,264 A | 2/2000 | Beffa et al. |
| 6,044,132 A | 3/2000 | Navab |
| 6,049,390 A | 4/2000 | Notredame |
| 6,049,582 A | 4/2000 | Navab |
| 6,072,177 A | 6/2000 | Mccroskey et al. |
| 6,088,423 A | 7/2000 | Krug et al. |
| 6,091,422 A | 7/2000 | Ouaknine et al. |
| 6,104,827 A | 8/2000 | Benn et al. |
| 6,105,029 A | 8/2000 | Maddalozzo, Jr. et al. |
| 6,108,007 A | 8/2000 | Shochet |
| 6,108,576 A | 8/2000 | Alfano et al. |
| 6,123,733 A | 9/2000 | Dalton |
| 6,175,655 B1 | 1/2001 | George |
| 6,205,120 B1 | 3/2001 | Packer et al. |
| 6,219,061 B1 | 4/2001 | Lauer et al. |
| 6,226,005 B1 | 5/2001 | Laferriere |
| 6,236,704 B1 | 5/2001 | Navab et al. |
| 6,243,098 B1 | 6/2001 | Lauer et al. |
| 6,249,594 B1 | 6/2001 | Hibbard |
| 6,255,655 B1 | 7/2001 | McCroskey et al. |
| 6,264,610 B1 | 7/2001 | Zhu |
| 6,268,846 B1 | 7/2001 | Georgiev |
| 6,278,460 B1 | 8/2001 | Myers et al. |
| 6,282,256 B1 | 8/2001 | Grass et al. |
| 6,289,235 B1 | 9/2001 | Webber et al. |
| 6,304,771 B1 | 10/2001 | Yodh et al. |
| 6,320,928 B1 | 11/2001 | Vaillant et al. |
| 6,324,241 B1 | 11/2001 | Besson |
| 6,377,257 B1 | 4/2002 | Borrel |
| 6,377,266 B1 | 4/2002 | Baldwin |
| 6,384,821 B1 | 5/2002 | Borrel |
| 6,404,843 B1 | 6/2002 | Vaillant |
| 6,415,013 B1 | 7/2002 | Hsieh et al. |
| 6,470,067 B1 | 10/2002 | Harding |
| 6,470,070 B2 | 10/2002 | Menhardt |
| 6,473,793 B1 | 10/2002 | Dillon et al. |
| 6,475,150 B2 | 11/2002 | Haddad |
| 6,507,633 B1 | 1/2003 | Elbakri et al. |
| 6,510,241 B1 | 1/2003 | Vaillant et al. |
| 6,519,355 B2 | 2/2003 | Nelson |
| 6,526,305 B1 | 2/2003 | Mori |
| 6,557,102 B1 | 4/2003 | Wong et al. |
| 6,559,958 B2 | 5/2003 | Motamed |
| 6,591,004 B1 | 7/2003 | VanEssen et al. |
| 6,615,063 B1 | 9/2003 | Ntziachristos et al. |
| 6,633,688 B1 | 10/2003 | Nixon |
| 6,636,623 B2 | 10/2003 | Nelson et al. |
| 6,654,012 B1 | 11/2003 | Lauer et al. |
| 6,658,142 B1 | 12/2003 | Kam et al. |
| 6,664,963 B1 | 12/2003 | Zatz |
| 6,674,430 B1 | 1/2004 | Kaufman et al. |
| 6,697,508 B2 | 2/2004 | Nelson |
| 6,707,878 B2 | 3/2004 | Claus et al. |
| 6,718,195 B2 | 4/2004 | Van Der Mark et al. |
| 6,731,283 B1 | 5/2004 | Navab |
| 6,740,232 B1 | 5/2004 | Beaulieu |
| 6,741,730 B2 | 5/2004 | Rahn et al. |
| 6,744,253 B2 | 6/2004 | Stolarczyk |
| 6,744,845 B2 | 6/2004 | Harding et al. |
| 6,745,070 B2 | 6/2004 | Wexler et al. |
| 6,747,654 B1 | 6/2004 | Laksono et al. |
| 6,754,299 B2 | 6/2004 | Patch |

(56) References Cited

U.S. PATENT DOCUMENTS

| | | |
|---|---|---|
| 6,765,981 B2 | 7/2004 | Heumann |
| 6,768,782 B1 | 7/2004 | Hsieh et al. |
| 6,770,893 B2 | 8/2004 | Nelson |
| 6,771,733 B2 | 8/2004 | Katsevich |
| 6,778,127 B2 | 8/2004 | Stolarczyk et al. |
| 6,785,409 B1 | 8/2004 | Suri |
| 6,798,417 B1 | 9/2004 | Taylor |
| 6,807,581 B1 | 10/2004 | Starr et al. |
| 6,825,840 B2 | 11/2004 | Gritz |
| 6,825,843 B2 | 11/2004 | Allen et al. |
| 6,923,906 B2 | 8/2005 | Oswald et al. |
| 6,947,047 B1 | 9/2005 | Moy et al. |
| 6,978,206 B1 | 12/2005 | Pu |
| 7,003,547 B1 | 2/2006 | Hubbard |
| 7,006,101 B1 | 2/2006 | Brown et al. |
| 7,031,022 B1 | 4/2006 | Komori et al. |
| 7,034,828 B1 | 4/2006 | Drebin et al. |
| 7,039,723 B2 | 5/2006 | Hu |
| 7,050,953 B2 | 5/2006 | Chiang et al. |
| 7,054,852 B1 | 5/2006 | Cohen |
| 7,058,644 B2 | 6/2006 | Patchet et al. |
| 7,076,735 B2 | 7/2006 | Callegari |
| 7,098,907 B2 | 8/2006 | Houston et al. |
| 7,120,283 B2 | 10/2006 | Thieret |
| 7,133,041 B2 | 11/2006 | Kaufman et al. |
| 7,154,985 B2 | 12/2006 | Dobbs |
| 7,167,176 B2 | 1/2007 | Sloan et al. |
| 7,184,041 B2 | 2/2007 | Heng et al. |
| 7,185,003 B2 | 2/2007 | Bayliss et al. |
| 7,219,085 B2 | 5/2007 | Buck et al. |
| 7,242,401 B2 | 7/2007 | Yang et al. |
| 7,262,770 B2 | 8/2007 | Sloan et al. |
| 7,274,368 B1 | 9/2007 | Keslin |
| 7,299,232 B2 | 11/2007 | Stakutis et al. |
| 7,315,926 B2 | 1/2008 | Fridella et al. |
| 7,324,116 B2 | 1/2008 | Boyd et al. |
| 7,339,585 B2 | 3/2008 | Verstraelen et al. |
| 7,472,156 B2 | 12/2008 | Philbrick et al. |
| 7,502,869 B2 | 3/2009 | Boucher et al. |
| 7,506,375 B2 | 3/2009 | Kanda et al. |
| 7,552,192 B2 | 6/2009 | Carmichael |
| 7,609,884 B1 | 10/2009 | Stalling |
| 7,693,318 B1 | 4/2010 | Stalling |
| 7,701,210 B2 | 4/2010 | Ichinose |
| 7,778,392 B1 | 8/2010 | Bergman |
| 7,876,944 B2 | 1/2011 | Stalling |
| 7,889,895 B2 | 2/2011 | Nowinski |
| 7,899,516 B2 | 3/2011 | Chen et al. |
| 7,907,759 B2 | 3/2011 | Hundley |
| 7,956,612 B2 | 6/2011 | Sorensen |
| 7,983,300 B2 | 7/2011 | Vaughan et al. |
| 7,991,837 B1 | 8/2011 | Tahan |
| 7,995,824 B2 | 8/2011 | Yim |
| 8,107,592 B2 | 1/2012 | Bergman |
| 8,189,002 B1 | 5/2012 | Westerhoff |
| 8,319,781 B2 | 11/2012 | Westerhoff |
| 8,369,600 B2 | 2/2013 | Can et al. |
| 8,386,560 B2 | 2/2013 | Ma |
| 8,392,529 B2 | 3/2013 | Westerhoff |
| 8,508,539 B2 | 8/2013 | Vlietinck |
| 8,538,108 B2 | 9/2013 | Shekhar |
| 8,542,136 B1 | 9/2013 | Owsley et al. |
| 8,548,215 B2 | 10/2013 | Westerhoff |
| 8,775,510 B2 | 7/2014 | Westerhoff |
| 8,976,190 B1 | 3/2015 | Westerhoff |
| 9,019,287 B2 | 4/2015 | Westerhoff |
| 9,167,027 B2 | 10/2015 | Westerhoff |
| 9,299,156 B2 | 3/2016 | Zalis |
| 9,355,616 B2 | 5/2016 | Westerhoff |
| 9,454,813 B2 | 9/2016 | Westerhoff |
| 9,509,802 B1 | 11/2016 | Westerhoff |
| 9,524,577 B1 | 12/2016 | Westerhoff |
| 9,595,242 B1 | 3/2017 | Westerhoff |
| 10,038,739 B2 | 7/2018 | Westerhoff |
| 10,043,482 B2 | 8/2018 | Westerhoff |
| 10,070,839 B2 | 9/2018 | Westerhoff |
| 10,540,803 B2 * | 1/2020 | Westerhoff ............ A61B 6/466 |
| 2001/0026848 A1 | 10/2001 | Van Der Mark |
| 2002/0016813 A1 | 2/2002 | Woods et al. |
| 2002/0034817 A1 | 3/2002 | Henry et al. |
| 2002/0049825 A1 | 4/2002 | Jewett et al. |
| 2002/0080143 A1 | 6/2002 | Morgan et al. |
| 2002/0089587 A1 | 7/2002 | White et al. |
| 2002/0099290 A1 | 7/2002 | Haddad |
| 2002/0099844 A1 | 7/2002 | Baumann et al. |
| 2002/0120727 A1 | 8/2002 | Curley et al. |
| 2002/0123680 A1 | 9/2002 | Vailant |
| 2002/0138019 A1 | 9/2002 | Wexler |
| 2002/0150202 A1 | 10/2002 | Harding |
| 2002/0150285 A1 | 10/2002 | Nelson |
| 2002/0180747 A1 | 12/2002 | Lavelle et al. |
| 2002/0184238 A1 | 12/2002 | Chylla |
| 2002/0184349 A1 | 12/2002 | Manukyan |
| 2003/0001842 A1 | 1/2003 | Munshi |
| 2003/0031352 A1 | 2/2003 | Nelson et al. |
| 2003/0059110 A1 | 3/2003 | Wilt |
| 2003/0065268 A1 | 4/2003 | Chen et al. |
| 2003/0086599 A1 | 5/2003 | Armato |
| 2003/0103666 A1 | 6/2003 | Edie et al. |
| 2003/0120743 A1 | 6/2003 | Coatney et al. |
| 2003/0123720 A1 | 7/2003 | Launav et al. |
| 2003/0149812 A1 | 8/2003 | Schoenthal et al. |
| 2003/0158786 A1 | 8/2003 | Yaron |
| 2003/0176780 A1 | 9/2003 | Arnold |
| 2003/0179197 A1 | 9/2003 | Sloan et al. |
| 2003/0194049 A1 | 10/2003 | Claus et al. |
| 2003/0220569 A1 | 11/2003 | Dione |
| 2003/0220772 A1 | 11/2003 | Chiang et al. |
| 2003/0227456 A1 | 12/2003 | Gritz |
| 2003/0234791 A1 | 12/2003 | Boyd et al. |
| 2004/0010397 A1 | 1/2004 | Barbour et al. |
| 2004/0012596 A1 | 1/2004 | Allen et al. |
| 2004/0015062 A1 | 1/2004 | Ntziachristos et al. |
| 2004/0022348 A1 | 2/2004 | Heumann |
| 2004/0059822 A1 | 3/2004 | Jiang |
| 2004/0066384 A1 | 4/2004 | Ohba |
| 2004/0066385 A1 | 4/2004 | Kilgard |
| 2004/0066891 A1 | 4/2004 | Freytag |
| 2004/0078238 A1 | 4/2004 | Thomas et al. |
| 2004/0102688 A1 | 5/2004 | Walker |
| 2004/0125103 A1 | 7/2004 | Kaufman |
| 2004/0133652 A1 | 7/2004 | Miloushev et al. |
| 2004/0147039 A1 | 7/2004 | Van Der Mark |
| 2004/0162677 A1 | 8/2004 | Bednar |
| 2004/0170302 A1 | 9/2004 | Museth et al. |
| 2004/0210584 A1 | 10/2004 | Nir et al. |
| 2004/0215858 A1 | 10/2004 | Armstrong et al. |
| 2004/0215868 A1 | 10/2004 | Solomon et al. |
| 2004/0239672 A1 | 12/2004 | Schmidt |
| 2004/0240753 A1 | 12/2004 | Hu |
| 2005/0012753 A1 | 1/2005 | Karlov |
| 2005/0017972 A1 | 1/2005 | Poole et al. |
| 2005/0066095 A1 | 3/2005 | Mullick et al. |
| 2005/0088440 A1 | 4/2005 | Sloan et al. |
| 2005/0128195 A1 | 6/2005 | Houston et al. |
| 2005/0152590 A1 | 7/2005 | Thieret |
| 2005/0165623 A1 | 7/2005 | Landi et al. |
| 2005/0225554 A1 | 10/2005 | Bastos et al. |
| 2005/0231503 A1 | 10/2005 | Heng et al. |
| 2005/0239182 A1 | 10/2005 | Berzin |
| 2005/0240628 A1 | 10/2005 | Jiang et al. |
| 2005/0256742 A1 | 11/2005 | Kohan et al. |
| 2005/0259103 A1 | 11/2005 | Kilgard et al. |
| 2005/0270298 A1 | 12/2005 | Thieret |
| 2005/0271302 A1 | 12/2005 | Khamene et al. |
| 2006/0010438 A1 | 1/2006 | Brady et al. |
| 2006/0010454 A1 | 1/2006 | Napoli et al. |
| 2006/0028479 A1 | 2/2006 | Chun |
| 2006/0034511 A1 | 2/2006 | Verstraelen |
| 2006/0066609 A1 | 3/2006 | Iodice |
| 2006/0197780 A1 | 9/2006 | Watkins et al. |
| 2006/0214949 A1 | 9/2006 | Zhang |
| 2006/0239540 A1 | 10/2006 | Serra |
| 2006/0239589 A1 | 10/2006 | Omernick |

(56) References Cited

U.S. PATENT DOCUMENTS

| | | |
|---|---|---|
| 2006/0282253 A1 | 12/2006 | Buswell et al. |
| 2007/0005798 A1 | 1/2007 | Gropper et al. |
| 2007/0038939 A1 | 2/2007 | Challen |
| 2007/0046966 A1 | 3/2007 | Mussack |
| 2007/0067497 A1 | 3/2007 | Craft et al. |
| 2007/0092864 A1 | 4/2007 | Reinhardt |
| 2007/0097133 A1 | 5/2007 | Stauffer et al. |
| 2007/0116332 A1 | 5/2007 | Cai et al. |
| 2007/0127802 A1 | 6/2007 | Odry |
| 2007/0156955 A1 | 7/2007 | Royer, Jr. |
| 2007/0165917 A1 | 7/2007 | Cao et al. |
| 2007/0185879 A1 | 8/2007 | Roublev et al. |
| 2007/0188488 A1 | 8/2007 | Choi |
| 2007/0226314 A1 | 9/2007 | Eick et al. |
| 2007/0255704 A1 | 11/2007 | Baek et al. |
| 2007/0280518 A1 | 12/2007 | Nowinski |
| 2008/0009055 A1 | 1/2008 | Lewnard |
| 2008/0042923 A1 | 2/2008 | De Laet |
| 2008/0086557 A1 | 4/2008 | Roach |
| 2008/0115139 A1 | 5/2008 | Inglett et al. |
| 2008/0137929 A1 | 6/2008 | Chen et al. |
| 2008/0147554 A1 | 6/2008 | Stevens et al. |
| 2008/0155890 A1 | 7/2008 | Oyler |
| 2008/0174593 A1 | 7/2008 | Ham |
| 2008/0208961 A1 | 8/2008 | Kim et al. |
| 2008/0224700 A1 | 9/2008 | Sorensen |
| 2008/0281908 A1 | 11/2008 | McCanne et al. |
| 2008/0317317 A1 | 12/2008 | Shekhar |
| 2009/0005693 A1 | 1/2009 | Brauner et al. |
| 2009/0043988 A1 | 2/2009 | Archer et al. |
| 2009/0077097 A1 | 3/2009 | Lacapra et al. |
| 2009/0147793 A1 | 6/2009 | Hayakawa et al. |
| 2009/0208082 A1 | 8/2009 | Westerhoff et al. |
| 2009/0210487 A1 | 8/2009 | Westerhoff et al. |
| 2009/0225076 A1 | 9/2009 | Vlietinck |
| 2009/0245610 A1 | 10/2009 | Can et al. |
| 2009/0313170 A1 | 12/2009 | Goldner et al. |
| 2010/0054556 A1 | 3/2010 | Novatzky |
| 2010/0060652 A1 | 3/2010 | Karlsson |
| 2010/0123733 A1 | 5/2010 | Zaharia |
| 2010/0174823 A1 | 7/2010 | Huang |
| 2010/0272342 A1 | 10/2010 | Berman et al. |
| 2010/0278405 A1 | 11/2010 | Kakadiaris et al. |
| 2011/0044524 A1 | 2/2011 | Wang et al. |
| 2011/0112862 A1 | 5/2011 | Yu |
| 2012/0078088 A1 | 3/2012 | Whitestone et al. |
| 2012/0233153 A1 | 9/2012 | Roman et al. |
| 2013/0195329 A1 | 8/2013 | Canda |
| 2015/0213288 A1 | 7/2015 | Bilodeau et al. |
| 2016/0012181 A1 | 1/2016 | Massey |
| 2017/0011514 A1 | 1/2017 | Westerhoff |
| 2017/0346883 A1 | 3/2017 | Westerhoff |
| 2017/0098329 A1 | 4/2017 | Westerhoff |
| 2017/0104811 A1 | 4/2017 | Westerhoff |
| 2017/0178593 A1 | 6/2017 | Westerhoff |
| 2019/0378325 A1* | 12/2019 | Westerhoff ............ A61B 6/037 |

FOREIGN PATENT DOCUMENTS

| | | |
|---|---|---|
| EP | 0502187 | 9/1992 |
| EP | 0611181 | 8/1994 |
| EP | 0476070 | 8/1996 |
| EP | 0925556 | 6/1999 |
| EP | 0953943 | 11/1999 |
| EP | 0964 366 | 12/1999 |
| EP | 187340 | 3/2001 |
| EP | 2098895 | 9/2009 |
| EP | 2098994 | 9/2009 |
| WO | WO9016072 | 12/1990 |
| WO | WO9102320 | 2/1991 |
| WO | WO9205507 | 4/1992 |
| WO | WO9642022 | 12/1996 |
| WO | WO9810378 | 3/1998 |
| WO | WO9812667 | 3/1998 |
| WO | WO9833057 | 7/1998 |
| WO | WO0120546 | 3/2001 |
| WO | WO0134027 | 5/2001 |
| WO | WO0163561 | 8/2001 |
| WO | WO0174238 | 10/2001 |
| WO | WO0185022 | 11/2001 |
| WO | WO0241760 | 5/2002 |
| WO | WO02067201 | 8/2002 |
| WO | WO02082065 | 10/2002 |
| WO | WO03061454 | 7/2003 |
| WO | WO03088133 | 10/2003 |
| WO | WO03090171 | 10/2003 |
| WO | WO03098539 | 11/2003 |
| WO | WO04019782 | 3/2004 |
| WO | WO04020996 | 3/2004 |
| WO | WO04020997 | 3/2004 |
| WO | WO04034087 | 4/2004 |
| WO | WO04044848 | 5/2004 |
| WO | WO04066215 | 8/2004 |
| WO | WO04072906 | 8/2004 |
| WO | WO05071601 | 8/2005 |
| WO | WO09029636 | 3/2009 |
| WO | WO09067675 | 5/2009 |
| WO | WO09067680 | 5/2009 |
| WO | WO11065929 | 6/2011 |

OTHER PUBLICATIONS

PCT/EP2018/075744, Preliminary and International Search Reports, dated Feb. 1, 2019, 17 pages.
PCT/US2008/084282, Preliminary and International Search Reports, dated May 11, 2011, 7 pages.
PCT/US2005/000837, Preliminary and International Search Reports, dated May 11, 2005, 7 pages.
PCT/US2008/74397, Preliminary and International Search Reports, dated Dec. 3, 2008 , 7 pages.
PCT/US2008/84368, Preliminary and International Search Reports, dated Jan. 13, 2009, 7 pages.
PCT/EP2016/067886, Preliminary and International Search Reports, dated Jan. 17, 2017, 18 pages.
PCT/US2008/84376, Preliminary and International Search Reports, dated Jan. 12, 2009, 6 pages.

* cited by examiner

FIG. 3

Auto-Prior Rule Properties

Name: Prior Chest CR
User Levels: 
Comment: For any current chest study CR load prior CT or CR exams of the chest
Other: ☐ Disable  ☐ Overwrite system rule Current study must match all of the following:

| All of the following ◊ | | | |
|---|---|---|---|
| Modality ◊ | Contains Any Of ◊ | CR CT | [+] [-] |
| Any of the following ◊ | | | [+] [-] |
| Body Part Examined ◊ | Equals ◊ | CHEST | [+] [-] |
| Study Description ◊ | Contains Any Of ◊ | CHEST THORAX | [+] [-] |

Prior study must match all of the following:

| All of the following ◊ | | | |
|---|---|---|---|
| Modality ◊ | Contains Any Of ◊ | CR | [+] [-] |
| Any of the following ◊ | | | [+] [-] |
| Body Part Examined ◊ | Equals ◊ | CHEST | [+] [-] |
| Study Description ◊ | Contains Any Of ◊ | CHEST THORAX | [+] [-] |

[Save] [Cancel]

List of Auto-Prior Rules

Prior Chest CR

○ System   ⊙ User

[New Rule] [Move to System] [Delete Rule] [Properties...]

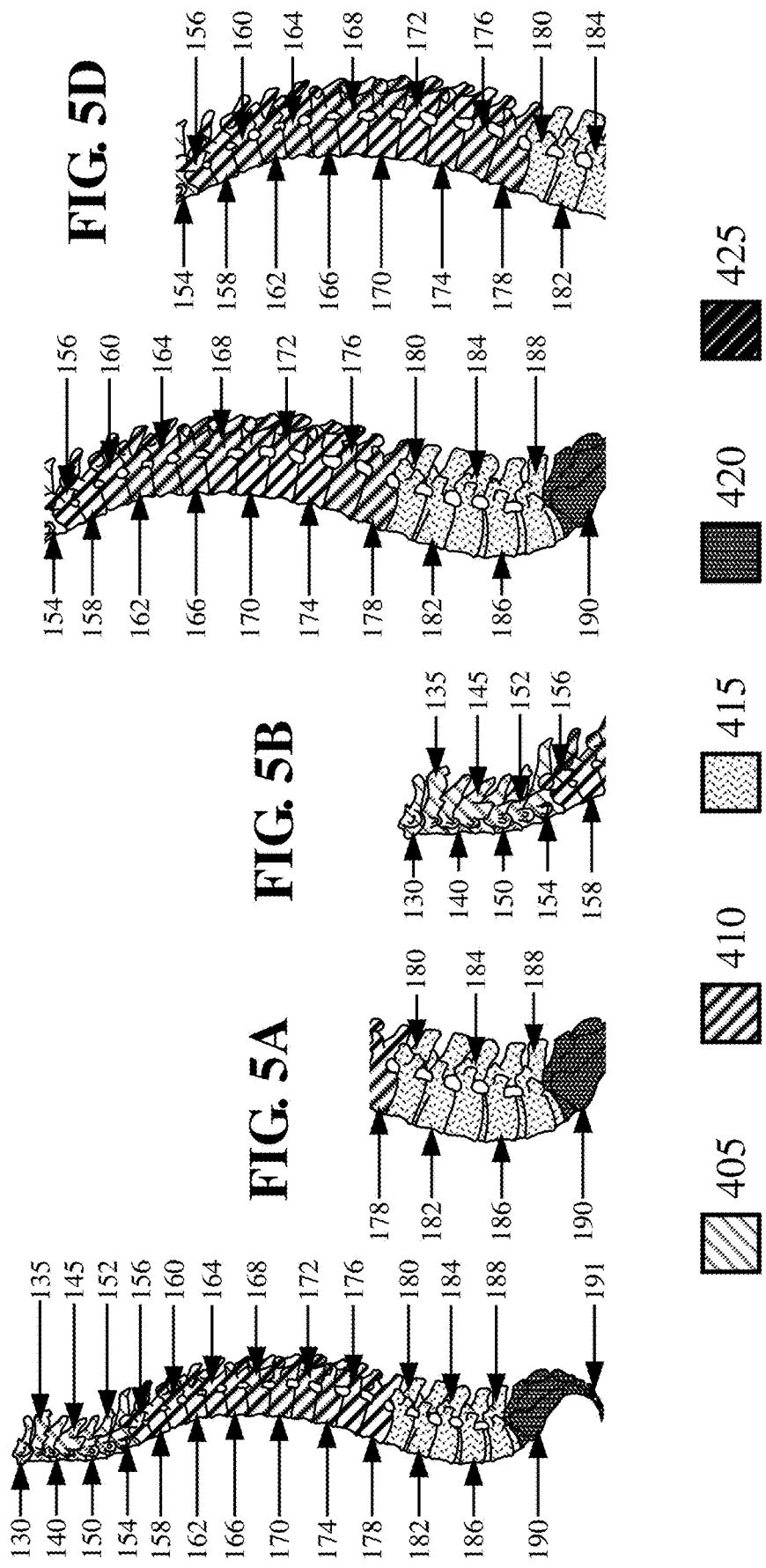

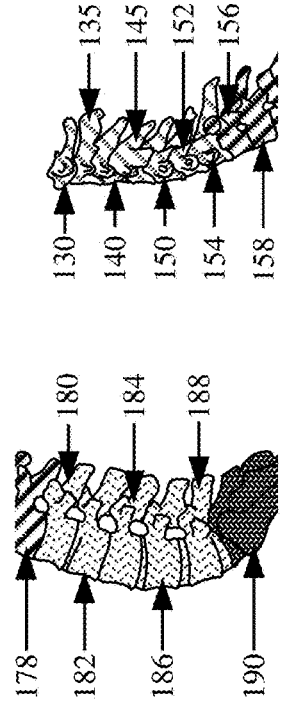
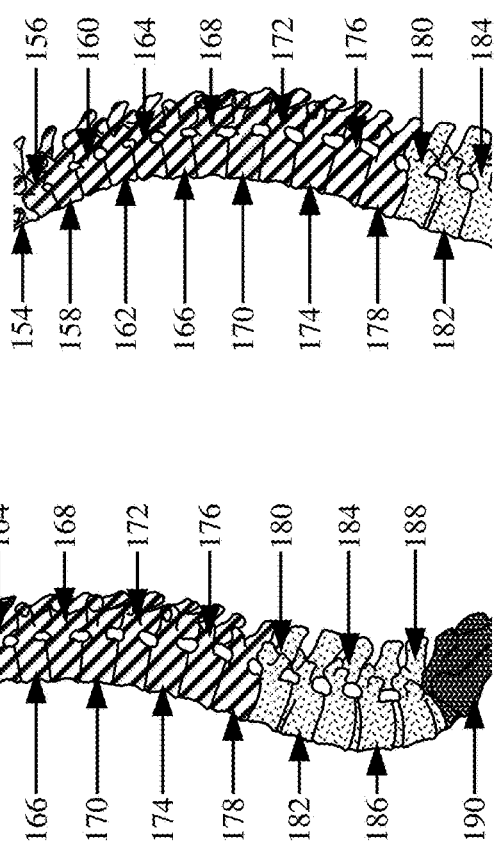
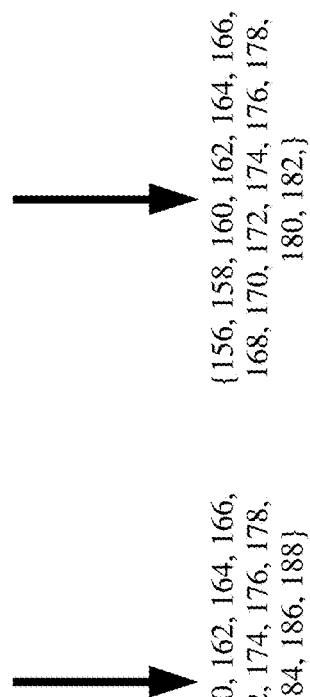

| Study | Modality | BodyPartExamined | Vertibrae |
|---|---|---|---|
| S1 | MR | LSPINE | {L1, L2, L3, L4, L5} |
| S2 | MR | SPINE | {C1, C2, C3, C4, C5, C6, C7, T1} |
| S3 | MR | SPINE | {T1, T2, T3, T4, T5, T6, T7, T8, T9, T10, T11, T12, L1, L2, L3, L4 L5} |
| S4 | MR | TSPINE | {T1, T2, T3, T4, T5, T6, T7, T8, T9, T10, T11, T12, L1, L2} |

FIG. 7

| Study | Selected |
|---|---|
| S2 | FALSE |
| S3 | TRUE |
| S4 | TRUE |

FIG. 8

METHOD AND SYSTEM FOR RULE BASED DISPLAY OF SETS OF IMAGES USING IMAGE CONTENT DERIVED PARAMETERS

PRIORITY CLAIM

This application claims the benefit of priority of (1) U.S. Provisional Patent Application Ser. No. 62/562,460, filed Sep. 24, 2017, (2) U.S. Provisional Patent Application Ser. No. 62/576,587, filed Oct. 24, 2017, and (3) U.S. Provisional Patent Application Ser. No. 62/712,912, filed Jul. 31, 2018. The teachings of (1)-(3) are herein incorporated by reference in their entireties and for all purposes.

BACKGROUND OF THE INVENTION

In order to diagnose a traditional X-Ray examination, the images printed on films would be 'hung' in front of a light box. For multi-image examinations, as well as for comparison with priors, the 'hanging' would often follow a specific protocol. For example, a particular organization or doctor may choose for a two-view chest X-Ray with a two-view prior exam, that the films be hung from left to right as follows: Frontal view of current examination, lateral view of current examination, frontal view of prior examination, lateral view of prior examination. In contrast, the doctor may hang mammography exams with the corresponding views of current and prior next to each other, if that was more appropriate for the diagnostic workflow in that case. Thus, the organization or doctor developed a traditional 'Hanging Protocol'. Currently, the film and the light box are often being replaced by computer systems, called PACS (Picture Archiving and Communication System). PACS systems can mimic the Hanging Protocols.

Traditional X-Ray examinations typically produce one or a small number of single two dimensional (2D) images. In contrast, the more advanced imaging modalities such as Computer Tomography (CT), Magnetic Resonance Imaging (MRI) or Positron Emission Tomography (PET) can produce dozens of series, each consisting of a hundred or more images. It is possible and not uncommon to review images from these advanced modalities in the same manner as traditional X-Ray images, i.e., by hanging the individual images side-by-side, either on a light-box or using a PACS system.

SUMMARY OF THE INVENTION

The invention pertains to digital data processing and, more particularly, by way of example, to the visualization of image data. Three dimensional (3D) and four dimensional (4D) image data is routinely acquired with CT, MRI, PET, confocal microscopes, 3D ultrasound devices, and other imaging devices. The medical imaging market is just one example of a market that uses these devices. The visualization of image data market is growing rapidly, with new CT scanners collecting larger amounts of data more quickly than previous generation CT scanners. The invention has application to areas including medical imaging, atmospheric studies, astrophysics and geophysics.

With the rapid increase in the amounts and types of information that can be acquired using imaging technology, we have identified a substantial problem with integrating different types of image-based information into a form that can be used by a diagnostician, for example a physician. Namely, although there may be many different types of image data, the forms, formats, integration, and display of relevant information is extremely difficult for a person to carry out without sophisticated computer processing. Embodiments of this invention therefore provide a computer-based analytic framework whereby image-based information from a variety of different sources can be integrated to provide increased ability to display relevant information, e.g., to display information for a physician to diagnose and evaluate a patient's condition. We have identified another substantial problem in the art, namely the increased likelihood of confusion of image-based information from different problems, e.g., a physician can incur increased likelihood of confusion of image-based information from different patients. In such situations, a diagnostician (e.g., physician) may be presented with image-based information from different patients. Such inadvertent conflation can produce misdiagnosis or mistaken non-diagnosis. In each case, the outcome can be serious, e.g., misdiagnoses of a patient can result in increased chance of morbidity and/or mortality.

In general aspects of this invention, a First Study is first selected for review by a physician or diagnostician. Selection of a Study will generally be based on some particular characteristic. Such characteristic can be anatomical, disease-based, or both. Once a First Study is selected, an Additional Candidate Study can be selected based on the anatomical location of the First Study. Therefore, if the First Study is a Chest X-Ray, an Additional Candidate Study can be a Chest CT scan, MRI, positron-emission tomography (PET) scan, or other image of the chest. Alternatively, if a First Study is an X-Ray image of the gastrointestinal tract, an Additional Candidate Study could be a series of X-Ray images taken after ingestion of a contrast agent (such as barium). It can be appreciated that such anatomically selected Additional Candidate Studies can be applied to any organ, organ system, or tissue.

Alternatively, Additional Candidate Studies can be selected based on the type of disorder or disease being evaluated. For example, in a case in which a patient has had a diagnosis of cancer of one organ (e.g., lung), it can be desirable for Additional Candidate Studies to be targeted to identification of metastases in another organ. Thus, if a First Study is a Chest X-Ray, an Additional Candidate Study can be of the lymphatic system, head and neck, or various abdominal quadrants. Such Additional Candidate Studies may be X-ray, CT scans, MRI scans, PET scans, vascular visualizations (e.g., with injected contrast media) or histological images taken during a biopsy. Because the degree of detail (i.e., "granularity") obtained using different imaging techniques may vary widely it can be desirable to have a Rule Based process whereby the granularity of an Additional Candidate Study is increased over that of the First Study.

For example, a Chest X-Ray is a two-dimensional image in which the entirety of the chest and lungs is represented as a flat image. An Additional Candidate Study could be a CT scan, where "2-dimensional" images are acquired at a series of different "depths" (e.g., "slices") through the organ. If the 2-dimensional images are of sufficient quality to produce a 3-dimensional image of the organ with desirable degree of granularity, then the Additional Candidate Study can be depicted and displayed along with the image of the First Study.

General Rule 1 for selecting an Additional Candidate Study therefore can be:

IF (Primary.Dicom.BodyPartExamined is "ANATOMICAL REGION 1", and Primary.Dicom.Modality=IMAGE TYPE 1")

THEN SELECT other studies for loading, WHERE (Other.Dicom.BodyPart Examined=ANATOMICAL REGION 1" and Other.Dicom.Modality="IMAGE TYPE 2").

If desired, in General Rule 1, Additional Candidate Studies can target "Other.Dicom.Modality="IMAGE TYPE 2").

It can be appreciated that any number of Additional Candidate Studies can be integrated using the computer-based processes of this invention.

Alternatively, General Rule 2 for selecting an Additional Candidate Study therefore can be:
 IF (Primary.Dicom.Disease is "DISEASE 1", and Primary.Dicom.Modality=IMAGE TYPE 1")
 THEN SELECT other studies for loading, WHERE (Other.Dicom.Disease="DISEASE 1" and Primary.Dicom.Modality="IMAGE TYPE 2").

It can be readily appreciated that application of General Rule 2 can integrate other Anatomical Regions and a number of different Image Types.

In an embodiment of the present invention, a method or system uses a rule derived basis to display image sets. In various embodiments of the present invention, the selection of the images to be displayed, the layout of the images, i.e., the hanging, as well as the rendering parameters and styles can be determined using a rule derived basis. In an embodiment of the present invention, the user is presented with images displayed based on their preferences without having to first manually adjust parameters. Accordingly, there is a time saving in not displaying images initially in a non-rule derived basis.

The parameters used in the rules can be derived from meta data stored in the data files, such as the DICOM parameters, but they can also be derived from the image content using one or more Convolutional Neural Networks (CNN). Each CNN is pre-trained to derive relevant aspects about the image. At the time of data ingestion, the CNN is applied to the images of the Study, and the output of the CNN is used to define Image Content Based parameters. Examples for such Image Content Based Parameters are (i) finer granular anatomic information, e.g. whether or not a particular organ is covered by a particular study, or (ii) whether or not a particular medical condition is present, such as a fracture or bleeding.

These and other aspects of the invention are evident in the drawings and in the description that follows.

BRIEF DESCRIPTION OF THE DRAWINGS

This invention is described with respect to specific embodiments thereof. Additional features can be appreciated from the Figures in which:

FIG. 3 shows an example of a user interface to specify rules including a dialog box to configure Study Selection rules, according to an embodiment of the invention.

FIG. 4 depicts a line drawing of an illustration of the human spine, with the vertebrae labeled according to standard terminology in human anatomy.

FIG. 5A is a line drawing of an illustration of Study S1 of a different part of the spine that may have been taken at different point in time to FIGS. 5B-5D. Study S1 is a scan of the lumbar spine containing all lumbar vertebrae L1, L2, L3, L4, and L5.

FIG. 5B is a line drawing of an illustration of Study S2 of a different part of the spine that may have been taken at different point in time to FIGS. 5A, 5C, and 5D. Study S2 is a scan of the cervical spine and does not contain any lumbar vertebrae.

FIG. 5C is a line drawing of an illustration of Study S3 of a different part of the spine that may have been taken at different point in time to FIGS. 5A, 5B, and 5D. Study S3 is a scan of vertebrae extending from lumbar to thoracic spine and also contains all five lumbar vertebrae (L1, L2, L3, L4, and L5).

FIG. 5D is a line drawing of an illustration of Study S4 of a different part of the spine that may have been taken at different point in time to FIGS. 5A-5C. Study S4 is a scan of the thoracic spine but it also contains lumbar vertebrae L1 and L2.

FIG. 6A is a line drawing corresponding to FIG. 5A and depicts the result of applying a particular neuronal network to Study S1 taken from one patient at a specific time, depicting different sections of the spine. The Image Content Based Parameter computed by the neuronal network in this example is the set (list) of vertebrae shown below the arrow, according to an embodiment of the present invention.

FIG. 6B is a line drawing corresponding to FIG. 5B and depicts the result of applying a particular neuronal network to Study S2 taken from one patient at a specific time, depicting different sections of the spine. The Image Content Based Parameter computed by the neuronal network in this example is the set (list) of vertebrae shown below the arrow, according to an embodiment of the present invention.

FIG. 6C is a line drawing corresponding to FIG. 5C and depicts the result of applying a particular neuronal network to Study S3 taken from one patient at a specific time, depicting different sections of the spine. The Image Content Based Parameter computed by the neuronal network in this example is the set (list) of vertebrae shown below the arrow, according to an embodiment of the present invention.

FIG. 6D is a line drawing corresponding to FIG. 5D and depicts the result of applying a particular neuronal network to Study S4 taken from one patient at a specific time, depicting different sections of the spine. The Image Content Based Parameter computed by the neuronal network in this example is the set (list) of vertebrae shown below the arrow, according to an embodiment of the present invention.

FIG. 7 depicts a subset of the DICOM tags and Image Content Based Parameters extracted from the Studies S1, S2, S3, S4 shown in FIG. 8, namely Modality, BodyPartExamined, and Vertebrae, according to an embodiment of the present invention.

FIG. 8 depicts an example for a Study Selection Rule according to an embodiment of the present invention. The Rule uses the Image Content Based Parameter Vertebrae. The table shows the result of the selection if Study S1 was loaded by a user as primary Study. Studies S3 and S4 would be selected for comparison, because they have common anatomy with the primary Study, and Study S2 would not be selected. As is obvious in this example, this could not be achieved using a rule based on the DICOM tag BodyPartExamined alone.

9A-9D, where FIG. 9C is one of two series of relevant prior studies identified by a Study Selection Rule as containing different but overlapping parts of the anatomy of the same patient, according to an embodiment of the present invention.

FIG. 9D is one of two series of relevant prior studies identified by a Study Selection Rule as containing different but overlapping parts of the anatomy of the same patient, according to an embodiment of the present invention.

DETAILED DESCRIPTION OF THE INVENTION

Definitions

Figure 1:
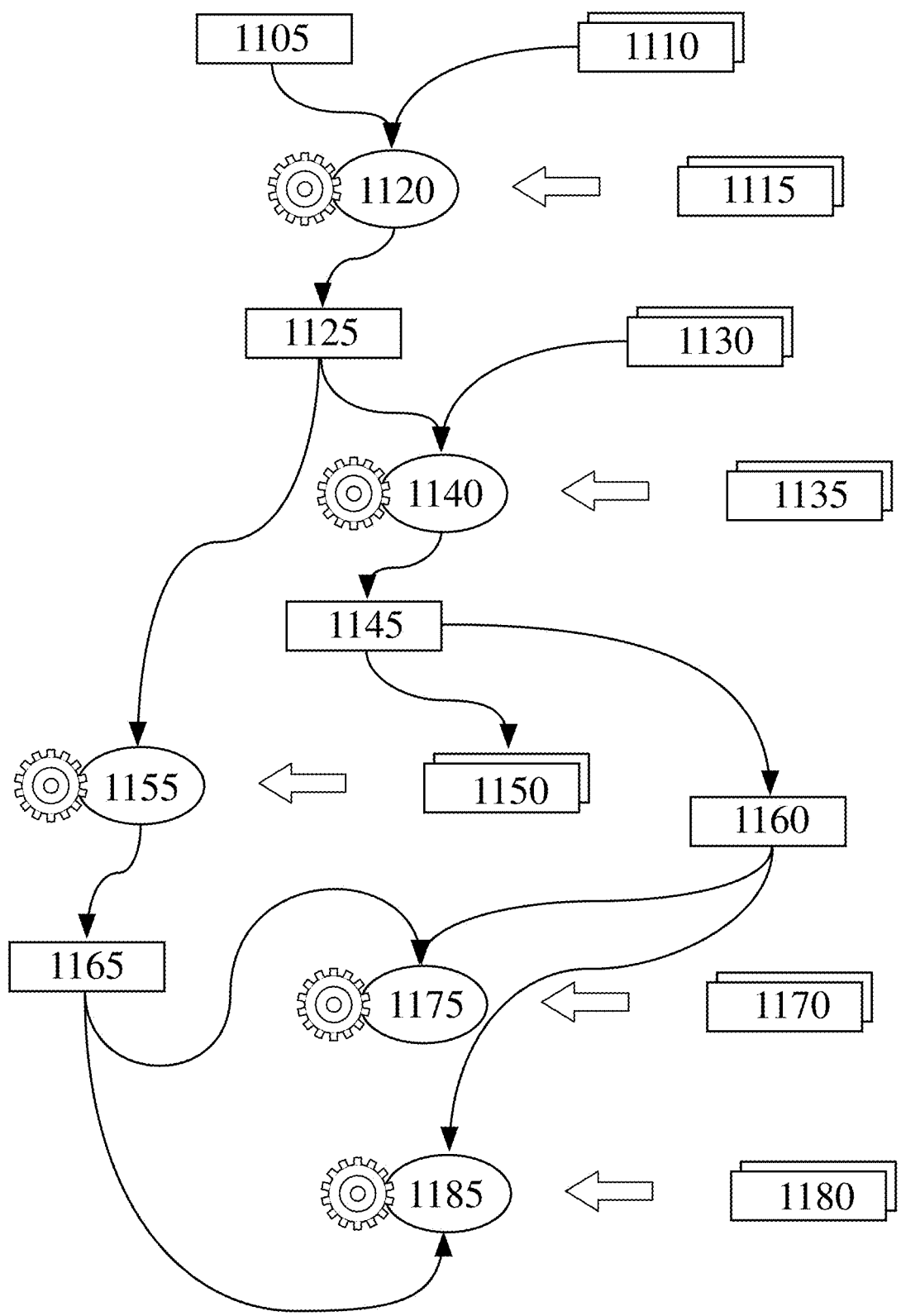
FIG. 1 depicts a flow chart showing the steps of applying various rules to the selected Study, according to an embodiment of the invention.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

The term "Study" will be used to refer to the set of images produced by an examination. A Study consists of one or more images. The images can be grouped into one or more image series. Each image, each series, and the whole Study can have different parameters attached. For medical images these can be defined by the Digital Imaging and Communication in Medicine (DICOM) standard.

Some or all of the images in a Study can form one or more three dimensional "Volumes." For 3D modalities, such as CT or MRI, often each individual image in the series corresponds to a volume, but that is not a requirement. For example a cardiac CT may contain multiple 3D volumes covering the heart, each corresponding to a different point in the cardiac cycle, and all of the images belonging to all of these volumes being grouped into the same series.

The term "Hanging Protocol" will be used to refer to specific conventions how X-Ray films are arranged (hung) at a light box.

The term "Display Protocol" will be used to refer to the way images are displayed in a computer system, specifically the selection of the images to be displayed, the layout of the images, as well as the rendering parameters and styles.

The term "View" will be used to refer to data corresponding to a digital image view of a Set of Images rendered with a given set of rendering parameters and rendering modes.

The term "Viewport" will be used to refer to the logical part of the screen on the client computer in which a particular View is displayed, for example the user interface on the client computer can contain four rectangular Viewports 1160 of which three show a frontal, left, and bottom view respectively of a particular data, while the fourth viewer might show a 2D cross section through the same or a different data set.

The term "Sets of Images" or "Image Set" will be used to refer to one or more images, selected based on the rules.

The term "Study Selection Rules" will be used to refer to the rules used to select the studies to be displayed.

The term "Protocol Selection Rules" will be used to refer to the rules used to select the layout of the images to be displayed.

The term "Image Set Rules" will be used to refer to the rules used to form Image Sets 1165 from the images of one or more Study by applying selection, sorting, and breaking rules.

The term "Style Rules" will be used to refer to the rules to determine which rendering type, rendering style, and rendering parameters are used for a particular Image Set 1165 in a particular viewer.

The term "Volume Rendering" will be used to refer to Volume Rendering techniques including shaded Volume Rendering techniques, maximum intensity projection (MIP), oblique slicing or multi-planar reformats (MPR), axial/sagittal and coronal slice display, and thick slices (also called slabs). In medical imaging, for example, Volume Rendering is used to display 3D images from 3D image data sets, where a typical 3D image data set is a large number of 2D slice images acquired by a CT or MRI scanner and stored in a data structure.

The term "anatomical characteristic" will be selected from the group consisting of one or more of spine, chest, abdomen, breast, shoulder, trapezius, arm, elbow, wrist, finger, pelvis, hip, fibula, knee, tibula, ankle, foot, neck, head, temporomandibular junction, face, brain, dentition, sinus, adrenals, retina, pituitary, and prostate. The anatomical characteristic can include the Body Part Examined. An anatomical characteristic can be either natural or pathologic. A natural anatomical characteristic of a patient would be the presence of seven cervical vertebrae. A pathologic anatomical characteristic of a patient would be the presence of only six cervical vertebrae.

The term "anatomical feature" refers to a medical condition, e.g., whether a fracture or bleeding is present in a given image or volume. An anatomical feature can be a fractured fibula, a herniated disc, urethral bleeding, e.g. bleeding with benign prostate hyperplasia, lacerated breast, Gun Shot Wound (GSW) to the chest, infection by *Treponema pertenue* giving rise to YAWS lesion in left distal leg. An anatomical feature is pathologic. In an embodiment of the invention, if ParameterA is fibula then the anatomical feature can be a fractured fibula.

The term "disease based characteristic" can be selected from the type of disorder or disease being evaluated, e.g., a diagnosis of lung cancer. The disease based characteristic can include the Body Part Examined. A disease based characteristic is pathologic.

The phrase "carried out using Convolutional Neural Networks" means that CNN is used to select or identify based on an anatomical characteristic ParameterZ. For example, when ParameterZ is SPINE, other secondary studies with the same anatomical characteristic can be selected and CNN can generate one or more ImageContentBased parameters from one or more of these secondary studies. The presence of the ImageContentBased parameters can be used to generate a final list for display. This way the rule would not select a cervical spine scan for comparison when the current study is a lumbar spine, but it could select a prior thoracic spine scan for comparison, if that scan did have an overlap with the current scan of the lumbar spine.

Overview

Often, the traditional 'Hanging Protocol' is either not intuitive, cannot display the information in a manner in which it can be reviewed or is not the most efficient way to display images. Alternative ways of rendering the acquired images can be more efficient or more appropriate for displaying the information. Examples include Volume Rendering techniques or maximum intensity projections of stacks of cross-sectional images, rendering of oblique slices, rendering of thick slices or slabs, or rendering of fused images (e.g. in PET/CT). Specialized diagnostic workstations that are often specific to a clinical application area are used to provide appropriate rendering of the acquired images. As organizations and doctors require better and faster visualization methods that allow users to interact with the image data in real-time, the requirements and demands for displaying the data will increase.

Figure 2:
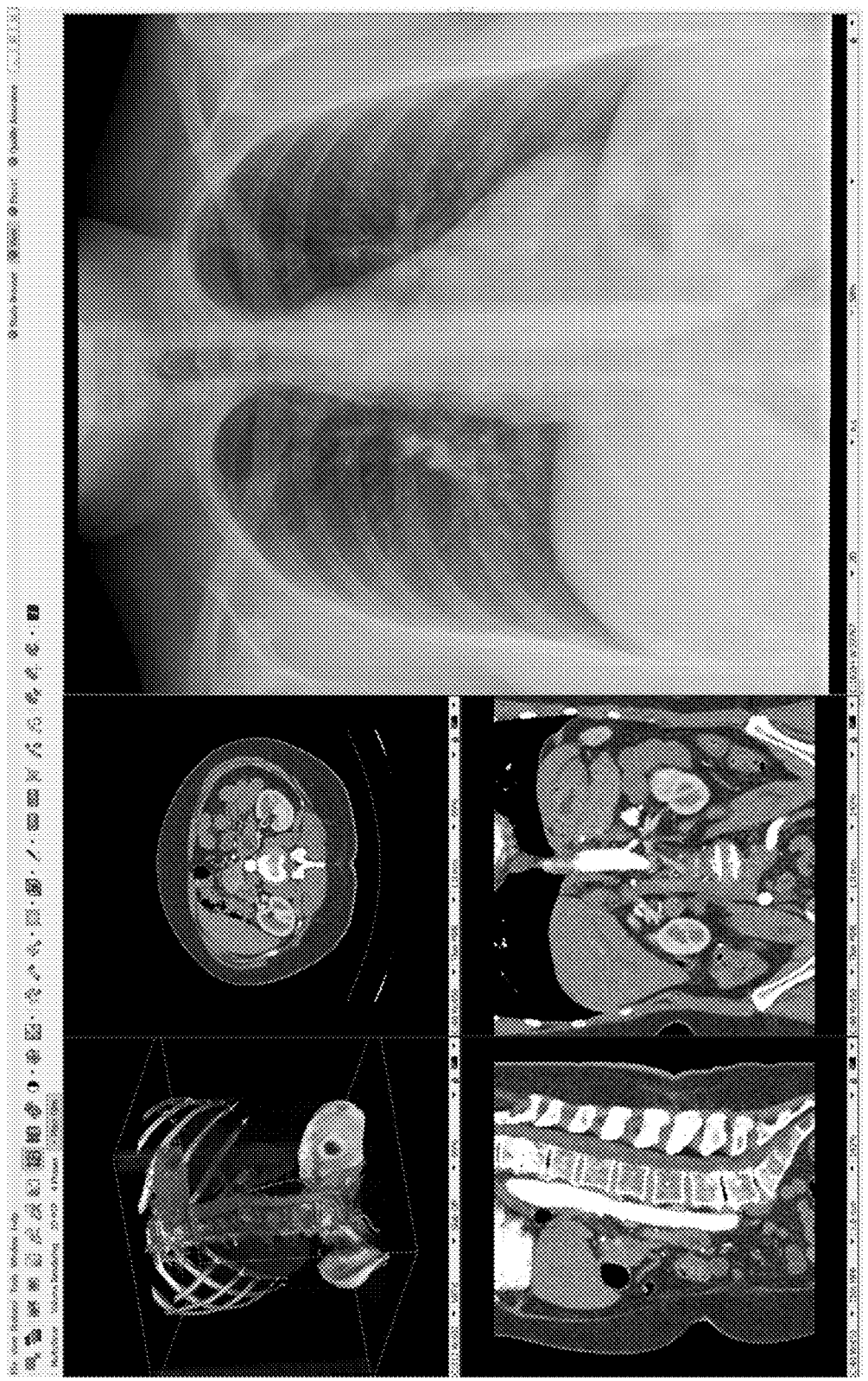
FIG. 2 depicts the resulting display for an example study, according to an embodiment of the invention.

FIG. 2 depicts an example study where the rules have created two Sets of Images. One Set of Images consists of a series of CT images forming a 3D volume, which is depicted in a volume rendered style in the Viewport 1160 in the upper left and in three orthogonal cross sections in the three other viewports in the left half of the screen. The second Set of Images consist of one chest X-Ray, assigned to a single Viewport 1160 covering the right half of the screen and rendering the X-Ray in 2D style. Appropriate data windows have been chosen by the rules to highlight the vasculature in the 3D rendering, as this is a study with contrast, as the rules can determine by the StudyDescription containing the word 'contrast'.

FIG. 1 is a flow chart showing how the rules are used to create the two Sets of Images shown in FIG. 2. As shown in FIG. 1, a primary Study 1105 which can be manually selected by a user. In step (i) 1120, based on Study Selection Rules 1115 which interrogate parameters in the primary Study 1105 such as DICOM Parameters and Abstract Tags of both the primary Study 1105 and the candidate studies 1110, the Study Selection Rules 1115 can identify additional candidate studies 1110. The second set of studies 1125 which includes the candidate studies 1110 and the primary Study 1105 are available to be loaded into Viewports 1160. In step (ii) 1140, the Protocol Selection Rules 1135 select a Display Protocol 1145 from the Available Display Protocols 1130 based on DICOM Parameters and Abstract Tags present in the second studies 1125. In step (iii) 1155, Image Set Rules 1150 are used to define a plurality of Image Sets 1165 from the second studies 1125. The one or more Viewports 1160 are defined in the Display Protocol 1145. In step (iv) 1175, Viewport Assignment Rules 1170 assign one or more Image Sets 1165 to one or more Viewports 1160. In step (v) 1185, Style Rules 1180 define a rendering style and rendering parameters. In an embodiment of the invention steps (i) through (v) are performed by a server processor running a render server program with an interface shown in FIG. 3 in which the rules (Study Selection Rules 1115, Protocol Selection Rules 1135, Image Set Rules 1150, Viewport Assignment Rules 1170, and the one or more Style Rules 1180) are used to automatically select and display the Image Sets 1165 in the Viewports 1160.

A render server program is described in U.S. application Ser. No. 13/831,967, entitled "Multi-User Mult-GPU Render Server Apparatus and Methods", inventors M. Westerhoff et al., which was filed Mar. 15, 2013, is herein expressly incorporated by reference in its entirety. A rule based render server program is described in U.S. application Ser. No. 13/831,982, entitled "Method and System for Transferring Data to Improve Responsiveness when Sending Large Data Sets", inventors D Stalling et al., which was filed Mar. 15, 2013, is herein incorporated by reference in its entirety.

The system can be connected to a network, e.g. in a hospital, with data being sent to the system from Imaging Modalities, such as CT Scanners or an X-Ray machine, from other computer systems, such as an image archive or PACS system, e.g. using the DICOM network protocol and file format or other suitable network protocols, such as HTTP, HTTPS, SMB and other suitable file formats, such as TIFF, PNG, JPEG. Data can also be inserted into the system by using a CD or DVD, or a USB Memory Stick or other portable media. The system can also query other systems, such as an image archive, and retrieve data, using suitable network protocols and file formats, such as DICOM, or WADO.

We refer to the process of a new imaging study being sent to or retrieved by the system as "Study Insertion" in the following.

At the time of Study Insertion for each Study, the images and the volumes of the Study are being processed individually by one or more Convolutional Neural Network (CNN). Separate CNNs can be used for images and volumes respectively, and pre-selection rules can be used to determine which images or volumes to process with which CNN. For example, the DICOM tag Modality can be used to process CT images with a different CNN than MRI images. The term "Study Selection Parameters" will be used to refer to one or more parameters chosen from the group of DICOM Parameters, Abstract Tags, and Image Content Based Parameters.

The term "Convolutional Neural Network," "CNN," or the like refer, in the usual and customary sense, to a class of deep, feed-forward artificial neural networks that has successfully been applied to analyzing e.g., visual imagery. Exemplary references disclosing methods and systems for CNN include: Alex Krizhevsky et al., *ImageNet Classification with Deep Convolutional Neural Networks*, In: ADVANCES IN NEURAL INFORMATION PROCESSING SYSTEMS 25 (Eds. F. Pereira, C. J. C. Burges, L. Bottou and K. Q. Weinberger), Curran Associates, Inc., 2012, pp. 1097-1105; and Christian Szegedy et al, *Going Deeper with Convolutions*, In: COMPUTER VISION AND PATTERN RECOGNITION (CVPR), 2015, each of which is incorporated herein by reference and for all purposes.

The parameters used in the rules can be derived from an image content using one or more CNN. In an embodiment of the present invention, CNN can be used in the context of localization and object detection. In an embodiment of the present invention, a CNN consists of an input layer, one or more hidden layers and an output layer. In an embodiment of the present invention, optimizing the performance of a CNN can be accomplished by increasing the depth or the number of levels of the network and its width or the number of units at each level. In an embodiment of the present invention, the width defines the region of space within which visual stimuli affect the firing of a single neuron or the receptive field. Given the availability of a large amount of labeled training data it is possible to train higher quality models. However, increased layers and/or widths typically means a larger number of parameters, which makes the enlarged CNN prone to overfitting, and increased use of computational resources. In an embodiment of the present invention, the depth and width of the CNN can be maximized, while constraining the computational requirement. In an embodiment of the present invention, an additional 1×1 convolutional layers can be added to the receptive field. In an alternative embodiment of the present invention, an additional n×n convolutional layers can be added to the receptive field. In an embodiment of the present invention, filters can be used to reduce the dimension and thereby constrain computational demands. In an alternative embodiment of the present invention, the outputs of multiple nodes at one layer can be combined into a single node in the next layer to constrain the computational demands. In an embodiment of the present invention, a resulting matrix of the CNN would include sparse clustering between regions of dense clustering. In an embodiment of the present invention, reconfiguring a matrix containing sparse clustering between regions of dense clustering into two or more relatively dense submatrices can be used to constrain the computational demands. In an embodiment of the present invention, maxpooling in which a matrix is partitioned into a set of non-overlapping submatrices and the maximum for each submatrix is output can be used to constrain the computational demands. In an embodiment of the present invention, filtering is followed by rectified linear activation. In an embodiment of the present invention, if the probability distribution of the data-set is representable by a large, very sparse CNN, then the optimal network topology can be constructed layer by layer by analyzing the correlation statistics of the activations of the previous layer and clustering neurons with highly correlated outputs and the institution of multi-scale processing. In an embodiment of the present invention, each CNN is pre-trained to produce one or more output channels that represent relevant aspects of the input images or volumes. These output channels of the CNNs are referred to as "Image Content Based Parameters" in the following. At the time of data ingestion, the CNN is applied to the images of the Study. In an embodiment of the present invention, the output of the CNN is used to define Image Content Basedparameters. In an embodiment of the present invention, an Image Content Based Parameter includes finer granular anatomic information. In an embodiment of the present invention, an Image Content Based Parameter includes whether a particular organ is covered by a particular study. In an embodiment of the present invention, an Image Content Based Parameter includes whether a particular medical condition is present. In an embodiment of the present invention, an Image Content Based Parameter includes a fracture. In an embodiment of the present invention, an Image Content Based Parameter includes a fracture of a specific bone. In an embodiment of the present invention, an Image Content Based Parameter includes a fracture of a tibia. In an embodiment of the present invention, an Image Content Based Parameter includes bleeding. In an embodiment of the present invention, an Image Content Based Parameter includes arterial bleeding. In an embodiment of the present invention, an Image Content Based Parameter includes arterial bleeding. In an embodiment of the present invention, an Image Content Based Parameter includes external venal bleeding. In an embodiment of the present invention, an Image Content Based Parameter includes internal venal bleeding. In an embodiment of the present invention, an Image Content Based Parameter includes venal bleeding. In an embodiment of the present invention, an Image Content Based Parameter includes external venal bleeding. In an embodiment of the present invention, an Image Content Based Parameter includes internal venal bleeding. In an embodiment of the present invention, an Image Content Based Parameter includes varicose internal venal bleeding. As can be appreciated by a person of ordinary skill Image Content Based Parameter can cover a variety of medical conditions and their anatomic locations.

FIG. 4 depicts an illustration of the human spine, with the vertebrae (C1 130, C2 135, C3 140, C4 145, C5 150, C6 152, C7 154, Th1 156, Th2 158, Th3 160, Th4 162, Th5 164, Th6 166, Th7 168, Th8 170, Th9 172, Th10 174, Th11 176, Th12 178, L1 180, L2 182, L3 184, L4 186, L5 188, Os sacrum 190 and coccyx 191) labeled according to standard terminology in human anatomy. Note that any labels and any grayscale coding (405 corresponds with cervical vertebrae, 410 corresponds with thoracic vertebrae, 415 correspond with lumbar vertebrae, 420 corresponds with sacrum and 425 corresponds with the coccyx) in FIG. 4, and FIGS. 5A-5D are schematic representations and are not present in any original images. FIG. 5A depicts Study S1, FIG. 5B depicts Study S2, FIG. 5C depicts Study S3, and FIG. 5D depicts Study S4 showing different parts of the spine that may have been taken at different time points. FIG. 5A depicts an illustration of Study S, a scan of the thoracic-sacrum region of the spine containing a portion of a thoracic vertebra 178, all lumbar vertebrae L1 180, L2 182, L3 184, L4 186, and L5 188, and a portion of the sacrum 190. FIG. 5B depicts an illustration of Study S2, a scan of the cervical spine showing cervical vertebrae C1 (Atlas) 130, C2 (Axis) 135, C3 140, C4 145, C5 150, C6 152, C7 154, Th1 156, and a portion of Th2 158. FIG. 5B does not contain any lumbar vertebrae. FIG. 5C depicts an illustration of Study S3, a scan of vertebrae extending from lumbar to sacral regions of the spine including a portion of C7 154, Th1 156, Th2 158, Th3 160, Th4 162, Th5 164, Th6 166, Th7 168, Th8 170, Th9 172, Th10 174, Th11 176, Th12 178, L1 180, L2 182, L3 184, L4 186, L5 188, and portion of Os sacrum 190. FIG. 5C contains all five lumbar vertebrae (L1 180, L2 182, L3 184, L4 186, and L5 188). FIG. 5D depicts an illustration of Study S4, a scan of the thoracic and lumbar regions of the spine including a portion of C7 154, Th1 156, Th2 158, Th3 160, Th4 162, Th5 164, Th6 166, Th7 168, Th8 170, Th9 172, Th10 174, Th11 176, Th12 178, L1 180, L2 182 and a portion of L3 184. In an embodiment of the invention, applying a Convolutional Neuronal Network (CNN) to Study S1 results in FIG. 6A which corresponds to FIG. 5A which recognizes L1 180, L2 182, L3 184, L4 186, and L5 188 in Study S1 and outputs the Image Content Based Parameters {L1, L2, L3, L4, L5}. In an embodiment of the invention, applying a Convolutional Neuronal Network (CNN) to Study S2 results in FIG. 6B which corresponds to FIG. 5B which recognizes C1 (Atlas) 130, C2 (Axis) 135, C3 140, C4 145, C5 150, C6 152, C7 154, Th1 156 in Study S2 and outputs the Image Content Based Parameters {C1, C2, C3, C4 C5, C6, C7, T1}. In an embodiment of the invention, applying a Convolutional Neuronal Network (CNN) to Study S3 results in FIG. 6C which corresponds to FIG. 5C which recognizes Th1 156, Th2 158, Th3 160, Th4 162, Th5 164, Th6 166, Th7 168, Th8 170, Th9 172, Th10 174, Th11 176, Th12 178, L1 180, L2 182, L3 184, L4 186, L5 188 in Study S3 and outputs the Image Content Based Parameters {T1, T2, T3, T4 T5, T6, T7, T8, T9, T10, T11, T12, L1, L2, L3, L4 L5}. In an embodiment of the invention, applying a Convolutional Neuronal Network (CNN) to Study S4 results in FIG. 6D which corresponds to FIG. 5D which recognizes Th1 156, Th2 158, Th3 160, Th4 162, Th5 164, Th6 166, Th7 168, Th8 170, Th9 172, Th10 174, Th11 176, Th12 178, L1 180, L2 182 in Study S4 and outputs the Image Content Based Parameters {T1, T2, T3, T4 T5, T6, T7, T8, T9, T10, T11, T12, L1, L2}. That is, based on the image the CNN recognizes vertebrae and outputs the Image Content Based Parameters. In an embodiment of the invention, these Image Content Based Parameters can then be used to select which of Studies S2, S3 and S4 can help a medical practitioner who has measured Study S1 make appropriate comparisons and diagnoses. For example, since the CNN analysis of Study S1 was able to recognize L1 180, L2 182, L3 184, L4 186, and L5 188 in Study S1 and output Image Content Based Parameters {L1, L2, L3, L4, L5} the medical professional can be interested in displaying other studies that display the lumber vertebra L1, L2, L3, L4, L5. As summarized in FIG. 7, the CNN analysis of Study S2 did not recognize lumber vertebra L1, L2, L3, L4, L5. In contrast, the CNN analysis of Study S3 did recognize lumber vertebra L1, L2, L3, L4, L5 and the CNN analysis of Study S4 did recognize lumber vertebra L1, L2. As such the CNN analysis identifies Primary.ImageContentBasedParameter="ParameterC" and Other.ImageContentBasedParameter="ParameterD", to be used in the Study Selection Rule:

IF (Primary.Dicom.AnatomicalCharacteristic= "ParameterA"),
THEN SELECT other studies for loading WHERE (Other.Dicom.AnatomicalCharacteristic="ParameterA" AND INTERSECTION(ParameterC,ParameterD) NOT EMPTY), which rule is fulfilled for primary Study S1, by study S3 and study S4, but not study S2, provided that the primary Study anatomical characteristic is the same in study S3 and study S4.

Figure 8:
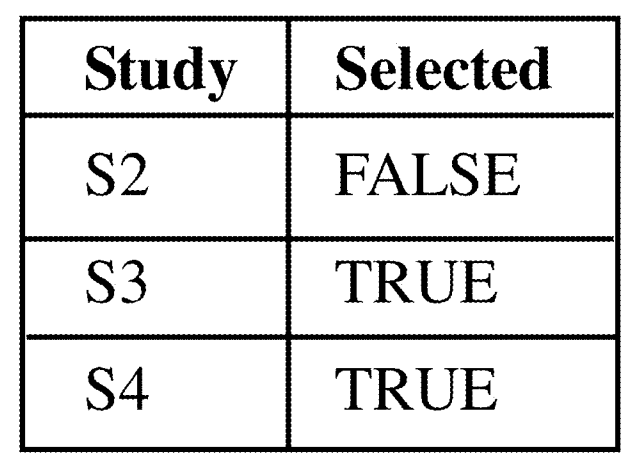

Note that any labels and any grayscale coding (405 corresponds with cervical vertebrae, 410 corresponds with thoracic vertebrae, 415 correspond with lumbar vertebrae, 420 corresponds with sacrum and 425 corresponds with the coccyx) in FIG. 6 are not present in any original images. FIG. 6A shows that of the labeled vertebra 178, 180, 182, 184, 186, 188, and 190 all lumbar vertebrae 180, 182, 184, 186, and 188 appear as labeled by arrow. FIG. 6B shows that all of the labeled vertebra 130, 135, 140, 145, 150, 152, 154, 156, and 158 appear as labeled by arrow. FIG. 6C shows that of the labeled vertebra 154, 156, 158, 160, 162, 164, 166, 168, 170, 172, 174, 176, 178, 180, 182, 184, 186, 188, and 190 appearing as labeled by arrow are 156, 158, 160, 162, 164, 166, 168, 170, 172, 174, 176, 178, 180, 182, 184, 186, and 188. FIG. 6D shows that of the labeled vertebra 154, 156, 158, 160, 162, 164, 166, 168, 170, 172, 174, 176, 178, 180, 182, and 184 appearing as labeled by arrow are 156, 158, 160, 162, 164, 166, 168, 170, 172, 174, 176, 178, 180, and 182. The Image Content Based Parameter computed by the neuronal network in this example is the set (list) of vertebrae shown below the arrow. FIG. 8 depicts an example for a Study Selection Rule according to an embodiment of the present invention. The Study Selection Rule is as follows:

IF (Primary.Dicom.BodyPartExamined="SPINE" and Primary.Dicom.Modality "MR")
THEN SELECT other studies for loading WHERE (Other.Dicom. BodyPartExamined="SPINE" and (Other.Dicom.Modality="MR") AND INTERSECTION(Primary.Vertebrae,Other.Vertebrae) NOT EMPTY).

Figures 9A, 9B, 9C, 9D:
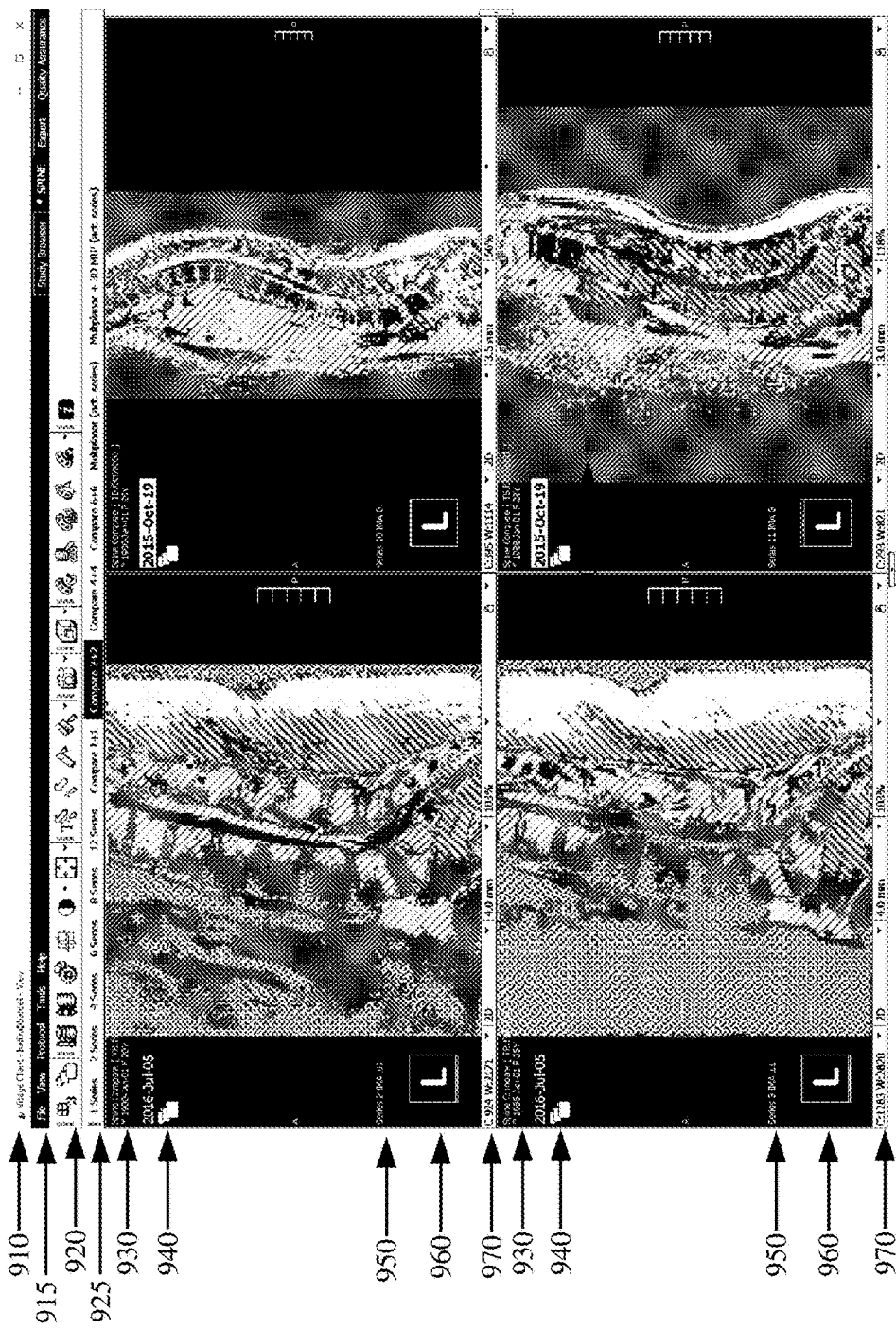
FIG. 9A is a line drawing of a current study which has been loaded by a user into an exemplary hanging protocol showing FIGS. 9A-9D.
FIG. 9B is a line drawing of a current study which has been loaded by a user into an exemplary hanging protocol showing FIGS. 9A-9D.
FIG. 9C is a line drawing of a prior study which has been loaded into an exemplary hanging protocol showing FIGS.
FIG. 9D is a line drawing of a prior study which has been loaded into an exemplary hanging protocol showing FIGS. 9A-9D, where

The Rule uses the Image Content Based Parameter 'Vertebrae'. FIG. 8 shows the result of the selection if Study S1 was loaded by a user as primary Study. Studies S3 and S4 would be selected for comparison, because they have common anatomy with the primary Study, and Study S2 would not be selected. As is obvious in this example, this could not be achieved using a rule based on the DICOM tag BodyPartExamined alone (e.g., LSPINE, SPINE and TSPINE). FIG. 7 depicts a subset of the DICOM tags and Image Content Based Parameters extracted from the Studies S1, S2, S3, S4 shown in FIG. 8, namely Modality, BodyPartExamined, and Vertebrae, according to an embodiment of the present invention. FIGS. 9A-D depict an exemplary hanging protocol where the client view is shown at 910, a menu including the functions 'File', 'View', 'Protocol', 'Tools' and 'Help' is shown at 915, as series of self-explanatory icons related to specific functions is shown at 920, the number of series including '1 Series', '2 Series', '4 Series', '6 Series', '8 Series', '12 Series', 'Compare 1+1', 'Compare 2+2', 'Compare 4+4', 'Compare 6+6', 'Multiplanar (act. series)', 'Multiplanar+3D MIP (act. series)' to be viewed is selected at 925, where the identification of the image displayed is shown at 930, the date of analysis of the image displayed is shown at 940, the series identification and image identification of the image displayed is shown at 950, and the anatomical location descriptor (L=lateral) of the image displayed is shown at 960, and the scale and magnification of the view of the image displayed is shown at 970. FIGS. 9A and 9B show two series of a current study that have been loaded by the user and where a Study Selection Rule has identified a relevant prior study containing a different but overlapping part of the anatomy of the same patient and displays FIGS. 9C and 9D, two series of the prior study for comparison (592 includes diaphragm, 593 includes disks, 594 includes the posterior spinal cord, 596 includes anterior spinal cord and vertebrae, 597 includes diaphragm and vertebrae and 598 includes the epithelial layer), according to an embodiment of the present invention.

In embodiments, each CNN is pre-trained to produce one or more output channels that represent relevant aspects of the input images or volumes. These output channels of the CNNs are referred to herein as "Image Content Based Parameters". Image Content Based Parameters can be anatomical parameters. For example, they can be more fine granular than the information stored in DICOM parameters. For example the DICOM parameter BodyPartExamined may specify "SPINE", whilst an Image Content Based Parameters can be defined for each vertebrae, such as L1, L2, L3 and so forth for the first, second, and third vertebrae in the lumbar spine. Image Content Based Parameters can also be defined for medical conditions, such as whether a fracture or bleeding is present in a given image or volume.

The Image Content Based Parameters computed for a Study are stored in an appropriate form, e.g. in a database, a text file, or as private DICOM tags.

As is easily appreciated, Image Content Based Parameters can also be computed at a later time than Study Insertion, e.g. by a scheduled task once every hour, or at the time of loading the study by the user.

Study Selection Rules 1115

In an embodiment of the present invention, based on the Study that the user selects for display (primary Study 1105), the system can first apply user defined rules to determine additional studies to be displayed together with the primary Study 1105. Such additional studies can be prior examinations that are relevant for the diagnosis of the current Study, or additional current studies. For example, a PET examination will often be looked at together with a CT examination acquired at the same time. The set of rules are constructed as follows:

Each rule consists of a matching criterion for the primary Study 1105 (primary condition), as well as matching criteria for additional studies (secondary condition). The matching criterion is an expression consisting of operators that allow evaluating the parameters of the Study and comparing them to defined values. The parameters of the Study can be any parameters defined by the DICOM standard, such as Study Description, Study Date, Modality, Patient Age, as well as any other parameters that can be derived from the DICOM parameters or from the Study itself, such as number of images, or number of image series as well as Image Content Based Parameters. The operators are numeric or string based operators, such as equals, greater than, less than, contains, etc. Expressions can be combined using Boolean operators such as AND, OR, NOT. Operators can also contain more complex expressions, including user defined functions defined in an appropriate programming language, such as JavaScript or VisualBasic.

Once a primary Study 1105 has been selected for display, the primary condition of each rule is evaluated. Those rules that match, i.e., evaluate to "true" for the given primary Study 1105, will then be applied to all other studies that are available for the same patient. Those other studies for which the secondary condition matches will be added to the list of studies to be displayed.

The following rule illustrates the concept. This rule will automatically load prior Chest X-Rays or prior Chest CT if the primary Study 1105 is a Chest X-RAY.

Study Selection Rule 1:
IF (Primary.Dicom.BodyPartExamined="CHEST" and Primary.Dicom.Modality "CR")
THEN SELECT other studies for loading
WHERE (Other.Dicom. BodyPartExamined="CHEST" and (Other.Dicom.Modality="CR" or Other.Dicom.Modality="CT")).

The rule is expressed in pseudo-code with the primary condition specified in the IF-clause and the secondary condition expressed in the SELECT-clause.

Study Selection Rule 2A:
IF (Primary.Dicom.BodyPartExamined="SPINE" and Primary.Dicom.Modality "MR")
THEN SELECT other studies for loading
WHERE (Other.Dicom. BodyPartExamined="SPINE" and (Other.Dicom.Modality="MR" AND INTERSECTION(Primary.Vertebrae,Other.Vertebrae) NOT EMPTY).

Study Selection Rule 2B:
IF (Primary.Dicom.BodyPartExamined="SPINE" and Primary.Dicom.Modality="CT")
THEN SELECT other studies for loading
WHERE (Other.Dicom. BodyPartExamined="SPINE" and Other.Dicom.Modality="CT" AND INTERSECTION(Spinous.process,Cobb.angle) NOT EMPTY).

Study Selection Rule 3A:
IF (Primary.Dicom.BodyPartExamined="CHEST" and Primary.Dicom.Modality "MR")
THEN SELECT other studies for loading
WHERE (Other.Dicom. BodyPartExamined="CHEST" and Other.Dicom.Modality="MR" AND INTERSECTION(Spinous.process,Thyroid) NOT EMPTY).

Study Selection Rule 3B:
IF (Primary.Dicom.BodyPartExamined="CHEST" and Primary.Dicom.Modality "CT")
THEN SELECT other studies for loading
WHERE (Other.Dicom. BodyPartExamined="CHEST" and Other.Dicom.Modality="CT" AND INTERSECTION(Spinous.process,Thyroid) NOT EMPTY).

Study Selection Rule 4A:
IF (Primary.Dicom.BodyPartExamined="BREAST" and Primary.Dicom.Modality "MR")
THEN SELECT other studies for loading
WHERE (Other.Dicom. BodyPartExamined="BREAST" and Other.Dicom.Modality="MR" AND INTERSECTION(Implant,Tumor) NOT EMPTY).

Study Selection Rule 4B:
IF (Primary.Dicom.BodyPartExamined="BREAST" and Primary.Dicom.Modality "CT")
THEN SELECT other studies for loading
WHERE (Other.Dicom. BodyPartExamined="BREAST" and Other.Dicom.Modality="CT" AND INTERSECTION(Implant,Tumor) NOT EMPTY).

Study Selection Rule 5A:
IF (Primary.Dicom.BodyPartExamined="BODY_PART" and Primary.Dicom.Modality="MR")
THEN SELECT other studies for loading
WHERE (Other.Dicom. BodyPartExamined="BODY_PART" and Other.Dicom.Modality="MR" AND INTERSECTION(Parameter1,Parameter2) NOT EMPTY).

Study Selection Rule 5B:
IF (Primary.Dicom.BodyPartExamined="BODY_PART" and Primary.Dicom.Modality="CT")
THEN SELECT other studies for loading
WHERE (Other.Dicom. BodyPartExamined="BODY_PART" and Other.Dicom.Modality="CT" AND INTERSECTION(Parameter3,Parameter4) NOT EMPTY).

Where Parameter3 can be but need not be equal to Parameter1 and Parameter4 can be but need not be equal to Parameter2.

Study Selection Rule 5C:
IF (Primary.Dicom.BodyPartExamined="BODY_PART" and Primary.Dicom.Modality="MG")
THEN SELECT other studies for loading WHERE (Other.Dicom. BodyPartExamined="BODY_PART" and (Other.Dicom.Modality="MG" AND INTERSECTION(Parameter5,Parameter6) NOT EMPTY).

Where Parameter5 can be but need not be equal to Parameter1 and/or Parameter3, and Parameter6 can be but need not be equal to Parameter2 and/or Parameter4.

In this example if Parameter5 is Primary.Vertebrae and Parameter6 is Other.Vertebrae the Parameter5 and Parameter6 denote the set of vertebrae in the primary and the other study respectively, and INTERSECTION( . . . ) NOT EMPTY selects only those prior studies for comparison that actually show at least parts of the same anatomy. This way the rule would not select a cervical spine scan for comparison when the current study is a lumbar spine, but it would select a prior thoracic spine scan for comparison, if that scan did have an overlap with the current scan of the lumbar spine.

Study Selection Rules: Normalization of DICOM Parameters

In an embodiment of the present invention, the rules can normalize DICOM parameters. As described above, a Study Selection Rule can contain arbitrary DICOM parameters. The DICOM standard specifies if a particular parameter is defined on a patient, Study, series, or image level. For example, a Study-level parameter should have the same value in all images of a Study, while a series-level parameter should have the same value in all images of a series. There are two problems related to assuming that this statement is always the case. Firstly, although a Study-level tag should have the same value for all images of a Study this is not always true. Secondly, some parameters are defined on a series- or image-level (e.g. modality is a series-level parameter) and therefore can be unavailable. In both cases it can be unclear what value is to be used when evaluating the rule. The invention described here provides different solutions to this problem.

In an embodiment of the present invention, a first approach is to choose a reference image and to read the value of a particular DICOM parameter from the reference image. The reference image can be: (i) the image that was inserted into the system first, (ii) the image with the oldest image content date, (iii) the image that was inserted into the system last, or (iv) the image with the earliest image content date. The choice of which image is to be chosen as the reference image can be configured for each parameter separately.

In an embodiment of the present invention, a second approach is to only allow original images to be chosen as the reference image. Non-viewable DICOM objects like structured reports, key objects, or presentation states are disregarded, as well as derived images such as secondary capture images or reformatted images.

In an embodiment of the present invention, a third approach is to provide a list of all distinct values that a particular DICOM parameter has in the images of a Study. In a Study Selection Rule one can then check if that list contains a particular value. The example above can then read as follows:

Study Selection Rule 6:
IF (Primary.Dicom.BodyPartExamined="CHEST" and Primary.DicomList.Modality contains "CR")
THEN SELECT other studies for loading WHERE (Other.Dicom.BodyPartExamined="CHEST" and (Other.DicomList.Modality contains "CR" or Other.DicomList.Modality contains "CT")).

Study Selection Rules: Abstract Tags

In an embodiment of the present invention, the Study Selection Rules 1115 contain other derived parameters such as Abstract Tags and/or Image Content Based Parameters that characterize a Study in addition to or instead of DICOM parameters. Abstract tags that are useful within Study Selection Rules 1115 include the following:

(i) RelativeStudyAge indicates relative age of Study in days compared to primary Study 1105.
(ii) PriorIndex indicates an index that enumerates all other studies from youngest to oldest.
(iii) NumImages indicates number of images in Study.
(iv) NumSeries indicated number of image series in Study.
(v) Num3DVolumes indicates number of 3D volumes in Study.
(vi) Num4DSequences indicates number of 4D sequences in Study (e.g. Cardiac CT).
(vii) HasReport indicates a flag that indicates if a report is available for a Study.
(viii) HasThinSliceVolumes indicates whether the study has at least one set of images that form a true 3D volume, i.e. a sufficiently large number of equidistant slices (the exact number can be user configurable, e.g. 30 would be a common choice) and a sufficiently small spacing between two consecutive slices to guarantee an isotropic (or close to isotropic) (again, this parameter can be user defined, values between 1 mm and 3 mm are common thresholds for CT and MR examinations).

For example, a rule that applies to a Mammogram Study and that selects at maximum three prior Mammogram studies no older than five years can read as follows.

Study Selection Rule 7:
IF (Primary.Dicom.Modality="MG"
THEN SELECT other studies for loading WHERE (Other.Dicom.Modality="MG" and Other.Abstract.PriorIndex<=3 and Other.Abstract.RelativeStudyAge<5*365).

Protocol Selection Rules 1135

In an embodiment of the present invention, once the studies to be displayed are determined as described above, a suitable display protocol can be selected. This is done using matching rules. Each matching rule consists of conditions that are applied to the primary and other studies to be loaded. Like in Study Selection Rules 1115, protocol selection rules may contain DICOM parameters (either taken from a reference image or provided as a list of distinct values gathered from all images of a study), as well as Abstract Tags and/or Image Content Based Parameters and user-defined functions. Each matching rule has a score and an associated display protocol.

In an embodiment of the present invention, all matching rules are evaluated and the display protocol of the matching rule that evaluates to true can be selected. If multiple matching rules evaluate to true, the one with the highest score can be selected.

The following example rule illustrates a matching rule that can apply for PET/CT studies of the abdomen to select a protocol named "StandardPetCTProtocol1" with a score of 10.

Protocol Selection Rule 1:
IF (Primary.Dicom.BodyPartExamined="ABDOMEN" and Primary.Dicom.Modality="CT" and Exists (Other1) and Other1.Dicom.Modality="PET")
THEN SELECT "StandardPetCTProtocol1" with score=10.

In an embodiment of the present invention, the rule is expressed in pseudo-code with the matching condition specified in the IF-clause and the chosen protocol specified by the SELECT.

Image Set Rules 1150

In an embodiment of the present invention, once a display protocol is selected, further rules defined within the protocol are evaluated. The next step comprises creation of so-called image sets. An image set consists of images that are logically grouped together. Usually, an image set is represented by a single preview icon in the application. It is an image set that is loaded into a viewer or tiled viewer. Note that DICOM series also represent a logical grouping of images. However, often DICOM series are not well suited for hanging of images and viewing. For example, in Mammography a single DICOM series may contain images of both left and right breast, in MRI it may contain both T1 and T2 images, or in CT it may contain both a localizer image and a 3D image stack. In all these cases the DICOM series can be split into different logical image sets. On the other hand, multiple DICOM series may represent the phases of a single 4D cardiac data set. In this case all those series can be joined into a single logical image set.

In an embodiment, the logical image set is a 4D cardiac image set. In an embodiment, the individual images of the 4D cardiac image set are sorted in time to represent the temporal ordering of the cardiac cycle. In an embodiment, CNN is applied to the images of the 4D cardiac image in order to determine the presence of pathological indicators, e.g., myocardial infarction. In embodiments, evidence of pathological indicator is memorialized in one or more Image Content Based Parameters.

Thus the creation of image sets based on rules is a key component of the rule-based display system, specifically for the more advanced rendering techniques. For example, the rules-based display system is used to create image sets that are very similar to the rules described above in Study Selection Rules 1115 and Protocol Selection Rules 1135 sections. A rule is a Boolean expression that can contain DICOM parameters, Abstract Tags, Image Content Based Parameters, or used-defined functions that are based on the DICOM parameters, Abstract Tags, Image Content Based Parameters. Image set rules however, are applied to all images of a study that was selected for loading (and not to the study itself). Image-level parameters thus represent no problem and do not need to be normalized or otherwise treated specially. All images that match an image-set rule are grouped into a respective image set.

In an embodiment of the present invention, the following rule (expressed in pseudo-code) collects all images of a current CT study.

Image Set Rule 1:
IF (Dicom.Modality="CT" and Abstract.PriorIndex=0)
THEN CREATE image set with ID 1.

In an embodiment of the present invention, the resulting image sets can be assigned IDs or names that allow for referencing the image sets later in layout and display set rules. In the above example an image set with ID 1 was defined. If no image matches an image set rule, no such corresponding image set will be created.

Image Set Rules: Sorting

In an embodiment of the present invention, the order of images within an image set is an important aspect. It determines how images are shown when the user browses through the image set or how images are distributed into the tiles of a tiled viewer. In one embodiment of the present invention, in order to specify image sorting, the image set rules can contain an ordered list of sorting criteria. All images that are matched by a rule are sorted according to those criteria.

For example, the following rule collects all images of a current CT study and sorts them according to DICOM series number at first and DICOM instance/image number at second.

Image Set Rule 2:
IF (Dicom.Modality="CT" and Abstract.PriorIndex=0)
THEN CREATE image set with ID 1
   SORTED BY Dicom.SeriesNumber ORDER:=ascending
   SORTED BY Dicom.InstanceNumber ORDER:=ascending.

Image Set Rules: Splitting

In an embodiment of the present invention, sorting criteria can be extended by a split flag. With the split flag it is possible to create multiple image sets from a single image set rule. When the value of a sorting criterion with split flag set to true changes, sub-sequent images are automatically inserted into a new image set. The resulting image sets are automatically enumerated by a sub-level ID.

For example, the following rule essentially creates image sets that correspond to DICOM series, because all images with different series number will be split into different sets.

Image Set Rule 3:
IF (Dicom.Modality="CT" and Abstract.PriorIndex=0)
THEN CREATE image set with ID 1.x
   SORTED BY Dicom.SeriesNumber ORDER:=ascending SPLIT:=true
   SORTED BY Dicom.InstanceNumber ORDER:=ascending SPLIT:=false.

In applications where a CT has been measured, it can happen that a study contains both a soft-kernel series and a hard kernel series and both series have the same series number. In order to separate the images into different image sets the above rule can be extended by the following:

Image Set Rule 4:
IF (Dicom.Modality="CT" and Abstract.PriorIndex=0)
THEN CREATE image set with ID 1.x
   SORTED BY Condition.CTSoftTisseKernel SPLIT:=true
   SORTED BY Dicom.SeriesNumber ORDER:=ascending SPLIT:=true
   SORTED BY Dicom.InstanceNumber ORDER:=ascending SPLIT:=false.

Here, Condition.CTSoftTissueKernel denotes a user-defined Boolean condition that tests whether an image has a CT soft-tissue kernel. The actual implementation of this condition can for example evaluate the manufacturer (which is encoded in a DICOM parameter). Depending on its value the rule can evaluate further parameters to find out if an image was reconstructed using a soft-tissue kernel or not. Since this Boolean condition was used as a sorting criterion with the split flag set to true, all non-soft-kernel images can be put into an image set with ID 1.1 and all soft-kernel images can be put into an image set with ID 1.2 (unless the image set is further split and IDs like 1.3 or 1.4 are created).

Image Set Rules: More Abstract Tags

In an embodiment of the present invention, additional Abstract Tags and/or Image Content Based Parameters are used in image set rules. One example is a tag that identifies whether an image has already been put into an image set. In principle, a single image can be put into multiple image sets, but sometimes this should be avoided. This can be achieved by evaluating image set rules in a pre-defined order and introducing an Abstract AlreadyReferenced.

For example, in CT study that has a localizer image and a 3D image stack both stored in one DICOM series, one may want to create an image set, one for the localizer and one for the 3D image stack. Accordingly, the image set rules are defined as follows.

Image Set Rule 5 (Localizer):
IF (Dicom.Modality="CT" and Condition.IsLocalizer=true)
THEN CREATE image set with ID 1
   SORTED BY Dicom.SeriesNumber ORDER:=ascending SPLIT:=true
   SORTED BY Dicom.InstanceNumber ORDER:=ascending SPLIT:=false.

Image Set Rule 6 (Images):
IF (Dicom.Modality="CT" and Abstract.AlreadyReferenced=false)
THEN CREATE image set with ID 2
   SORTED BY Dicom.SeriesNumber ORDER:=ascending SPLIT:=true
   SORTED BY Dicom.InstanceNumber ORDER:=ascending SPLIT:=false.

Here Condition.IsLocalizer is a user-defined condition that returns true if an image is a localizer image, and false otherwise. In an embodiment of the present invention, Rule 1 is applied first. Therefore the localizer image is put into a separate image set with ID 1. Next rule 2 is applied. This rule can match for all CT images including the localizer image. However, because AlreadyReferenced=false is specified, the localizer image is skipped and not placed into image set 2.

In an embodiment of the present invention, the creation of the image sets based on rules is a key component of the efficient rules based display, specifically for the more advanced rendering techniques. For example rules can be used to identify sets of 2D images that together form a 3D volume.

Viewer Assignment Rules

In another embodiment of the present invention, a display protocol defines multiple viewers, each with one or more tiles, i.e., viewports. To each viewer one or more image sets can be assigned based on Viewer Assignment Rules that are similar to the protocol section rules described herein. Viewer Assignment Rules are defined in the display protocol. The rules determine which image set shall be initially shown in a viewer. In case multiple image sets are assigned to a viewer, the one with the highest score is chosen. Afterwards users may cycle quickly through the remaining image sets using dedicated tools (Previous/Next Image Set), or pick another image set from a special image set menu.

Like the other rule types Viewer Assignment Rules contain Boolean expressions of DICOM parameters, Abstract Tags, Image Content Based Parameters, or user-defined conditions based on DICOM parameters, Image Content Based Parameters, or Abstract Tags. In many cases it is sufficient to specify the image sets to be assigned to a viewer by their image set ID instead of evaluating the underlying DICOM parameters, Image Content Based Parameters and/or Abstract Tags again. Therefore, the image set ID is simply set as a separate Abstract Tag. In the following example the two rules load image sets with the IDs 1 and 2 into a viewer, but assign ID 1 a higher score so that this image set is initially visible (provided such an image set exists).

Viewer Assignment Rule 1:
IF (EXISTS ImageSet[1])
THEN Viewport[0].AddImageSet(ID=1, score=10).
Viewer Assignment Rule 2:
IF (EXISTS ImageSet[2])
THEN Viewport[0].AddImageSet(ID=2, score=5).

In an embodiment of the present invention, viewer assignment rules are applied to image sets. Thus there is a possible conflict regarding ambiguous image-level and series-level tags. This conflict is resolved in the same way as described herein in the Normalization of DICOM Parameters section. This means that values of DICOM parameters, Image Content Based Parameters, but also Abstract Tags, are automatically taken from some reference image. Alternatively, for all DICOM parameters a list of distinct values occurring in all images of the image set can be used in an assignment rule.

Style Rules

In one embodiment of the present invention, there is a final set of rules that specify the rendering style and other rendering parameters to be used when showing a particular image set. For example, for a CT Angiogram study, often a volume rendering style display (VRT) is desired, whereas for a study looking for lung nodules a maximum intensity projection (MIP) of 20 mm slabs may be desired. Style rules, that can be user specific, allow driving that automatically. The rules can use the same parameters as discussed above, as well as the existence or absence of certain image sets.

In one embodiment of the present invention, the system uses a global, ordered list of style rules that is evaluated independently for each viewer and each image set loaded into a viewer. An Abstract Tag DisplaySetID is provided that allows formulating style rules for a specific viewer or group of viewers.

Parameters driven by Style Rules include the following:
Rendering style (can be 2D, oblique, curved, MIP slab, 3D MIP, VRT, shaded VRT, etc.);
Image alignment (left, right, top, bottom, centered);
Inverse display (black on white versus white on black);
Colormap or transfer function;
Window/level (data window);
Slice thickness;
Zoom factor;
Camera position and orientation; and
Labels/OverlayDisplay of labels, annotations and other overlay elements.

The following is an example of a style rule that activates inverse 3D MIP rendering in all viewers with a DisplaySetID between 101 and 104, provided a PET data set is loaded into those viewers (modality PT, i.e., positron emission tomography). Also, an automatic window/level setting is used that is computed from the histogram of the image set (the 2% lowest values are all mapped to white, and the 2% highest values are all mapped to black):

Style Rule 1:
IF (Abstract.DisplaySetID>100 and
    Abstract.DisplaySetID<105 and
    Dicom.Modality="PT")
THEN SET
    RenderingStyle:="3D MIP"
    Inverse:=true
    DataWindow:="2% 98%"

The following is another example of a different style rule that always causes the image set with image set ID 200 to be displayed in MPR mode using 20 mm thick slices, with a window/level as specified in the DICOM parameters, and with a zoom factor so that the whole viewer window is filled out. The rule is as follows.

Style Rule 2:
IF (Abstract.ImageSetID=200)
THEN SET
    RenderingStyle:="MPR"
    SliceThickness:="20"
    DataWindow:="DICOM1"
    ZoomFactor:="FitToWindow"

Summary of Rule Types

Table I summarizes all types of rules that are applied in the rule-base display system:

TABLE I

| Rule Type | Applies to | Normalized Parameters | Defined where |
|---|---|---|---|
| Study Selection Rule | Studies | yes | globally |
| Protocol Selection Rule | Studies | yes | globally |
| Image Set Rule | Images | not required | protocol |
| Viewer Assignment Rule | Image Sets | yes | globally, protocol |
| Style Rule | Image Sets | yes | globally, protocol |

Described above are methods and systems for implementing a rule derived basis to display image sets. The foregoing description of embodiments of the methods, systems, and components of the present invention has been provided for the purposes of illustration and description. It is not intended to be exhaustive or to limit the invention to the precise forms disclosed. Many modifications and variations will be apparent to one of ordinary skill in the relevant arts. For example, steps performed in the embodiments of the invention disclosed can be performed in alternate orders, certain steps can be omitted, and additional steps can be added. The embodiments were chosen and described in order to best explain the principles of the invention and its practical application, thereby enabling others skilled in the art to understand the invention for various embodiments and with various modifications that are suited to the particular used contemplated. Other embodiments are possible and are covered by the invention. Such embodiments will be apparent to persons skilled in the relevant art(s) based on the teachings contained herein. The breadth and scope of the present invention should not be limited by any of the above-described exemplary embodiments, but should be defined only in accordance with the following claims and their equivalents.

Example Shown in FIG. 2

An example of how these aspects can be combined is shown in FIG. 2. In the example the user has selected a CT examination of the abdomen. The following rules have been used to determine that a recent X-Ray of the chest is relevant and shall be displayed as well:

IF (Primary.Dicom.BodyPartExamined="ABDOMEN" and Primary.Dicom.Modality="CT")
THEN SELECT other studies for loading WHERE (Other.Dicom. BodyPartExamined="ABDOMEN" OR Other.Dicom. BodyPartExamined="CHEST") and (Other.Dicom.Modality="CR" or Other.Dicom.Modality="CT") AND Other.RelativeStudyAge<"90 days"

From this rule, a hanging protocol can be selected. In the example the protocol selection rules determine that the CT study is a thin slice CT study (i.e. that it has image series that form a 3D volume with sufficient resolution in all directions to display volume rendering or non-axial slices in a meaningful way). Furthermore the example rule determines that this is a study with enhanced vasculature, by looking for the key words "contrast" or "angio" in the study description.

The display protocol selection rule that applies here and select the protocol CTThinSliceVesselWithPrior can read:
IF (Primary.Dicom.BodyPartExamined="ABDOMEN" and Primary.Dicom.Modality="CT" and Primary.Abstract.HasThinSliceVolumes and (Primary.Dicom.StudyDescription containsAnyOf "contrast, angio" and exists Other1 THEN SELECT "CTThinSliceVesselWithPrior" with score=10.

From this image sets are generated using Image Set Rules:
IF (Dicom.Modality="CT" and Abstract.PriorIndex=0 and Condition.IsPartOfThinSliceVolume and Condition.CTSoftTisseKernel)
THEN CREATE image set with ID 1.x
    SORTED BY Abstract.NumberOfSlicesInVolume ORDER:=descending SPLIT:=true
    SORTED BY Dicom.SeriesNumber ORDER:=ascending SPLIT:=true
    SORTED BY Dicom.Abstract.VolumeIndex ORDER:=ascending SPLIT:=true
    SORTED BY Dicom.Abstract.SlicePosition ORDER:=ascending SPLIT:=false.

This rule will actually form sets from images that contain images that are part of a ThinSliceVolume and that have been reconstructed with a "soft tissue" kernel. Given the protocol selection rule has specifically matched for just CT studies, the conditions Dicom.Modality="CT" and Abstract.PriorIndex=0 are actually redundant, but could be useful if a different selection rule was used.

The images will first be sorted by the size of the volume of which they are part (Abstract.NumberOfSlicesInVolume), then by DICOM series. The split parameter in this case will ensure that an image set contains images from on series only. A DICOM series can sometimes contain multiple non-consecutive volumes. The Abstract Tag VolumeIndex will then indicate for each image, which of those volumes it is part of. If a series contains only one volume, then this will be "1" for all images in the series. The split=true in this part of the rule would result in a separate image set for each of those volumes. Finally, within each volume, the images are ordered by slice position, but not split. This way we end up with one image set for each soft kernel thin slice volume, the largest volume being the first image set (ID 1.1). This ID will be used further in subsequent rules.

The rule to form an image set from any CR prior study in this example is much simpler:
IF (Dicom.Modality="CR" and Abstract.PriorIndex=1)
THEN CREATE image set with ID 10
    SORTED BY Dicom.SeriesNumber ORDER:=ascending SPLIT:=false
    SORTED BY Dicom.InstanceNumber ORDER:=ascending SPLIT:=false.

This creates one image set with ID=10 containing all images for the first prior study, if that is a CR.

In practice, additional rules, such as Image Set Rule 5 and 6 (see above) will be used to collect the remaining images of the primary Study 1105. The remaining images are not shown in the layout depicted in the example FIG. 2.

The Display Protocol 1145 contains multiple layouts. The one shown in FIG. 2 is defined as follows:

```
DEFINE Layout {
ID="Layout5";
NAME="+PlainFilm"
Viewports {
{ ID=50, Geometry="(0,0)-(0.25,0.5)"},
{ ID=51, Geometry="(0.25,0)-(0.5,0.5)"},
{ ID=52, Geometry="(0,0.5)-(0.25,1)"},
{ ID=53, Geometry="(0.25,0.5)-(0.5,0.5)"},
{ ID=54, Geometry="(0.5,0)-(1,1)", Style="2D"}
}
}
```

In this example the geometry is defined in a coordinate system having the origin in the upper left corner of the screen with the x axis pointing to the right and the y axis pointing down. Please note how parameters of the viewers can be set in the layout definition. Parameters can also be set or overridden in the assignment and style rules, as will be explained next.

In this example, viewer assignment and style rules are as follows:

```
IF ImageSetExists (1.1) and ImageSetExists(10) THEN
SHOW_LAYOUT Layout5 WITH
    Viewport[0].AddImageSet(1.1)
    Viewport [0].Style="VRT(diffuse)"
    Viewport [0].Colormap="CTAngioSoftTissue"
    Viewport [1,2,3].AddImageSet(1.1)
    Viewport [1,2,3].Style="MPR"
    Viewport [1,2,3].DataWindow="DICOM1"
    Viewport [1].oriantation="axial"
    Viewport [2].oriantation="sagittal"
    Viewport [3].oriantation="coronal"
    Viewport [4].AddImageSet(10)
    IF (ImageSet[10].Dicom.Columns > 1024) THEN
    Viewport[4].Zoom="FitToWindow"
    ELSE
    Viewport[4].Zoom="1:1"
```

In this particular example, the rule to select the layout is rather simple: It is shown if the two image sets used exist. This is because the criteria to construct these images sets have been rather specific. As will be appreciated, the proposed system gives this type of flexibility.

ASPECTS OF THE INVENTION

Some aspects of this invention include methods of displaying one or more Sets of Images comprising the steps of:
 a. selecting a primary Study;
 b. selecting one or more Study Selection Parameters based on the primary Study;
 c. selecting one or more Study Selection Rules based on the one or more Study Selection Parameters;
 d. selecting one or more Sets of Images from a plurality of images based on the one or more Study Selection Rules;
 e. selecting one or more Display Protocol Selection Parameters based on the one or more Sets of Images selected;

f. selecting one or more Display Protocol Selection Rules based on the one or more Display Protocol Selection Parameters;

g. selecting one or more Display Parameters using the one or more Display Protocol Selection Rules; and h. displaying the one or more Sets of Images according to the Display Parameters.

Additional aspects include methods one or more Display Parameter are selected from the group consisting of Image Set Selection Parameters and View and Viewport Selection Parameters.

Further aspects include methods where the one or more Display Parameters are selected from the group consisting of Image Set Selection Rules, View and Viewport Selection Rules, and Display Protocol Selection Rules.

Yet further aspects include methods where the step of identifying one or more Image Set Selection Rules is based on the one or more Image Set Selection Parameters.

Still further aspects include methods where the step of selecting one or more Viewpoint Selection Rules is based on one or more View and Viewport Selection Parameters.

Other aspects include methods where the step of displaying the one or more Sets of Images is based on one or more Display Protocol Selection Rules, one or more Image Set Selection Rules, and one or more View and Viewport Selection Rules.

Still other aspects include methods where one or more of the Study Selection Parameters are selected from the group consisting of DICOM parameters, Image Content Based Parameters, and Abstract Tags.

Other aspects include methods where one or more of the Display Protocol Selection Parameters are selected from the group consisting of DICOM parameters, Image Content Based Parameters, and Abstract Tags.

Additional aspects include methods where one or more of the Image Set Selection Parameters are selected from the group consisting of DICOM parameters, Image Content Based Parameters, and Abstract Tags.

Further aspects include methods where one or more of the View and Viewport Selection Parameters are selected from the group consisting of DICOM parameters, Image Content Based Parameters, and Abstract Tags.

More aspects include methods where one or more Study Selection Parameters are derived from a single reference image.

Still more aspects include methods where one or more Study Selection Parameters are derived from a single reference image DICOM Parameters.

Yet other aspects include methods where one or more Display Protocol Selection Parameters are derived using a list of all values of a DICOM parameter occurring in any of the one or more Sets of Images.

Alternative aspects include methods where the one or more View and Viewport Selection Rules contain protocols for one or more Viewports displaying images as 2D.

Other alternative aspects include methods where the one or more View and Viewport Selection Rules contain protocols for one or more Viewports displaying images in a 3D rendering mode.

Further alternative aspects include methods where one or more Study Selection Parameters include one or more Abstract Tags selected from the group consisting of RelativeStudyAge, PriorIndex. NumImages, NumSeries, Num3DVolumes, Num4DSequences and HasReport.

In other aspects, this invention includes methods where one or more View and Viewport Selection Rules include one or more Abstract Tags selected from the group consisting of Image Sets to be displayed, Rendering Style, Additional image sets for image fusion, Image Alignment, Colormap/Transfer Function, Slice Thickness, Zoom Factor, Camera position, Camera orientation and Labels/Overlay elements or one or more Image Content Based Parameters.

In still other aspects, this invention includes methods further comprising the steps of:
  receiving one or more Sets of Images based on the Study Selection Rules;
  selecting one or more Image Set Selection Parameters;
  selecting one or more Image Set Selection Rules based on the one or more Image Set Selection Parameters; and
  displaying the one or more Sets of Images based on the Display Protocol Selection Rules and the Image Set Selection Rules.

In another aspect, this invention includes methods of displaying one or more Sets of Images comprising the steps of:
  selecting one or more Study Selection Parameters;
  selecting or more Study Selection Rules based on the one or more Study Selection Parameters;
  receiving one or more Sets of Images based on the Study Selection Rules;
  selecting one or more Display Protocol Selection Parameters based on the one or more Sets of Images selected;
  selecting one or more Display Protocol Selection Rules based on the one or more Display Protocol Selection Parameters; and
  displaying the one or more Sets of Images based on the Display Protocol Selection Rules.

Another aspect of this invention includes methods of displaying images comprising the steps of:
  a. selecting one or more Study Selection Parameters;
  b. selecting Study Selection Rules based on the one or more Study Selection Parameters;
  c. receiving one or more images based on the Study Selection Rules;
  d. selecting one or more Display Protocol Selection Parameters based on the one or more images selected;
  e. selecting Display Protocol Selection Rules based on the one or more Display Protocol Selection Parameters;
  f. selecting one or more Image Set Selection Parameters;
  g. selecting Image Set Selection Rules based on the one or more Image Set Selection Parameters;
  h. selecting one or more View and Viewport Selection Parameters;
  i. selecting View and Viewport Selection Rules based on the one or more View and Viewport Selection Parameters; and
  j. displaying the one or more images based on the Display Protocol Selection Rules, the Image Set Selection Rules and the View and Viewport Selection Rules.

Other aspects of the invention include methods where the Study Selection Rule is:
  IF (Primary.Dicom.BodyPartExamined="CHEST" and Primary.Dicom.Modality "CR")
  THEN SELECT other studies for loading WHERE (Other.Dicom. BodyPartExamined="CHEST" and (Other.Dicom.Modality="CR" or Other.Dicom.Modality="CT")).

In another aspect, this invention includes methods where the Study Selection Rule is:
  IF (Primary.Dicom.BodyPartExamined="CHEST" and Primary.DicomList.Modality contains "CR")
  THEN SELECT other studies for loading WHERE (Other.Dicom.BodyPartExamined="CHEST" and (Other.DicomList.Modality contains "CR" or Other.DicomList.Modality contains "CT")).

In other aspects, this invention includes methods where the Study Selection Rule is:

IF (Primary.Dicom.Modality="MG"
  THEN SELECT other studies for loading WHERE (Other.Dicom.Modality="MG" and Other.Abstract.PriorIndex<=3 and Other.Abstract.RelativeStudyAge<5*365).

In yet another aspect, this invention includes methods where the Protocol Selection Rule is:

IF (Primary.Dicom.BodyPartExamined="ABDOMEN" and Primary.Dicom.Modality="CT" and Exists (Other1) and Other1.Dicom.Modality="PET")
  THEN SELECT "StandardPetCTProtocol1" with score=10.

In aspects of the invention, methods include an Image Set Rule:

IF (Dicom.Modality="CT" and Abstract.PriorIndex=0)
THEN CREATE image set with ID 1.

Additionally, other aspects include methods where the Image Set Rule is:

IF (Dicom.Modality="CT" and Abstract.PriorIndex=0)
THEN CREATE image set with ID 1
  SORTED BY Dicom.SeriesNumber ORDER:=ascending
  SORTED BY Dicom.InstanceNumber ORDER:=ascending.

Still other aspects include methods where the Image Set Rule is:

IF (Dicom.Modality="CT" and Abstract.PriorIndex=0)
THEN CREATE image set with ID 1.x
  SORTED BY Dicom.SeriesNumber ORDER:=ascending SPLIT:=true
  SORTED BY Dicom.InstanceNumber ORDER:=ascending SPLIT:=false.

Moreover, other aspects include methods where the Image Set Rule is:

IF (Dicom.Modality="CT" and Abstract.PriorIndex=0)
THEN CREATE image set with ID 1.x
  SORTED BY Condition.CTSoftTisseKernel SPLIT:=true
  SORTED BY Dicom.SeriesNumber ORDER:=ascending SPLIT:=true
  SORTED BY Dicom.InstanceNumber ORDER:=ascending SPLIT:=false.

Yet other aspects include methods where the Image Set Rule (Localizer) is:

IF (Dicom.Modality="CT" and Condition.IsLocalizer=true)
THEN CREATE image set with ID 1
  SORTED BY Dicom.SeriesNumber ORDER:=ascending SPLIT:=true
  SORTED BY Dicom.InstanceNumber ORDER:=ascending SPLIT:=false.

Other aspects of the methods of this invention include an Image Set Rule (Images):

IF (Dicom.Modality="CT" and Abstract.AlreadyReferenced=false)
THEN CREATE image set with ID 2
  SORTED BY Dicom.SeriesNumber ORDER:=ascending SPLIT:=true
  SORTED BY Dicom.InstanceNumber ORDER:=ascending SPLIT:=false.

Yet other aspects of the methods of this invention include using Image Set Rule (Images):

IF (Dicom.Modality="CT" and Abstract.AlreadyReferenced=false)
THEN CREATE image set with ID 2
  SORTED BY Dicom.SeriesNumber ORDER:=ascending SPLIT:=true
  SORTED BY Dicom.InstanceNumber ORDER:=ascending SPLIT:=false.

Additionally, other aspects include methods where the Display Parameters include Viewer Assignment Rule:

IF (Abstract.ImageSetID=1)
THEN SELECT image set with score=10.

Yet further aspects include methods where the Display Parameters include a Viewer Assignment Rule:

IF (Abstract.ImageSetID=2)
THEN SELECT image set with score=5.

Additional aspects include methods further comprising a Viewer Assignment Rule:

IF (Abstract.ImageSetID=2)
THEN SELECT image set with score=5.

Further Embodiments

Further embodiments contemplated herein include the following.

In an aspect, there is provided a method including: (a) selecting a primary Study of a patient selected from a plurality of studies; (b) selecting as a ParameterA an anatomical characteristic in the primary Study and a ParameterB as Modality in the primary Study; (c) executing on a server digital data processor a render server program which applies one or more Study Selection Rules to: (i) generate a list of a plurality of secondary studies based on ParameterA and ParameterB; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the one or more ImageContentBased parameters identified are present in the primary Study. In an embodiment, the one or more ImageContentBased parameters are vertebrae.

In an embodiment, the vertebrae in the primary Study are selected from the group consisting of L1, L2, L3, L4, and L5, and at least one of the vertebra in the secondary study is a vertebra present in the primary Study. In an embodiment, the vertebrae in the primary Study are selected from the group consisting of C1, C2, C3, C4, C5, C6, and C7, and at least one of the vertebra in the secondary study is a vertebra present in the primary Study. In an embodiment, the vertebrae in the primary Study are selected from the group consisting of Th1, Th2, Th3, Th4, Th5, Th6, Th7, Th8, Th9, Th10, Th11, and Th12, and at least one of the vertebra in the secondary study is a vertebra present in the primary Study. In an embodiment, the CNN is pretrained with the plurality of studies. In an embodiment, the CNN is pretrained with a first plurality of studies where the first plurality of studies is selected based on the anatomical characteristic in the primary Study. In an embodiment, the CNN is pretrained with a first plurality of studies where the first plurality of studies is selected based on one or more of the ImageContentBased parameters.

In an embodiment, the method further includes the CNN selecting based on psueudo code:
IF (Primary.Dicom.AnatomicalCharacteristic="SPINE" and Primary.Dicom.Modality="MR")
THEN SELECT other studies for loading
WHERE (Other.Dicom.AnatomicalCharacteristic="SPINE" and Other.Dicom.Modality "MR" AND INTERSECTION (Primary.Vertebrae,Other.Vertebrae) NOT EMPTY).

In an embodiment, the one or more Study Selection Rules restrict the final list to studies of the patient.

In another aspect, there is provided a method including: (a) selecting a primary Study of a patient selected from a plurality of studies; (b) selecting a ParameterA from the group consisting of an anatomical characteristic and a disease based characteristic in the primary Study; (c) executing on a server digital data processor a render server program which applies one or more Study Selection Rules to: (i) generate a list of a plurality of secondary studies based on ParameterA; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the method further includes selecting a ParameterB, where the plurality of secondary studies exclude one or more based on ParameterB. In an embodiment, ParameterB is Modality. In an embodiment, ParameterB is selected from the group consisting of Computer Tomography (CT), then the Modality in the two or more secondary studies inserted is selected from the group consisting of Computed Radiography (CR), Digital Radiography (DX), Mammography (MG), Magnetic Resonance (MR), Opthalmic Photography (OP), Positron Emission Tomography (PT), Radio Fluoroscopy (RF), and X-Ray Angiography (XA). In an embodiment, ParameterB in the primary Study is equal to the ParameterB in the secondary study.

In an embodiment, the method further includes where a Study Selection Rule of the one or more Study Selection Rules in step (c) requires
SELECT other studies for loading, WHERE INTERSECTION(Primary.Dicom.Modality,Other.Dicom.Modality) NOT EMPTY.

In an embodiment, ParameterA is BodyPartExamined. In an embodiment, ParameterA is selected from the group consisting of SPINE, CHEST, ABDOMEN, BREAST, SHOULDER, TRAPEZIUS, ARM, ELBOW, WRIST, FINGER, PELVIS, HIP, FIBULA, KNEE, TIBULA, ANKLE, FOOT, NECK, HEAD, TEMPOROMANDIBULAR JUNCTION, FACE, BRAIN, DENTITION, SINUS, ADRENALS, RETINA, PITUITARY, and PROSTATE.

In an embodiment, the one or more Study Selection Rules restrict the final list to studies of the patient. In an embodiment, the method further includes where a Study Selection Rule of the one or more Study Selection Rules in step (c) requires
SELECT other studies for loading, WHERE INTERSECTION(Primary.Dicom.Modality,Other.Dicom.Modality) NOT EMPTY.

In an embodiment, the ImageContentBased parameter is stored as a private DICOM tag.

In another aspect, there is provided a method including: (a) selecting a primary Study of a patient selected from a plurality of studies; (b) selecting as a ParameterA a disease-based characteristic in the primary Study and selecting as a ParameterB a Modality in the primary Study; (c) executing on a server digital data processor a render server program which applies one or more Study Selection Rules to: (i) generate a list of a plurality of secondary studies based on ParameterA and ParamaterB; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the one or more ImageContentBased parameters identified are present in the primary Study. In an embodiment, the one or more ImageContentBased parameters are vertebrae. In an embodiment, the vertebrae in the primary Study are selected from the group consisting of L1, L2, L3, L4, and L5, and at least one of the vertebrae in the secondary study is a vertebra present in the primary study. In an embodiment, the vertebrae in the primary Study are selected from the group consisting of C1, C2, C3, C4, C5, C6, and C7, and at least one of the vertebrae in the secondary study is a vertebra present in the primary Study. In an embodiment, the vertebrae in the primary Study are selected from the group consisting of Th1, Th2, Th3, Th4, Th5, Th6, Th7, Th8, Th9, Th10, Th11, and Th12, and at least one of the vertebrae in the secondary study is a vertebra present in the primary Study. In an embodiment, the CNN is pretrained with the plurality of studies. In an embodiment, the CNN is pretrained with a first plurality of studies where the first plurality of studies is selected based on the disease-based characteristic in the primary Study. In an embodiment, the CNN selects one or more secondary studies which show the same anatomy. In an embodiment, the one or more Study Selection Rules restrict the final list to studies of the patient.

In another aspect there is provided a method including: (a) selecting a primary Study of a patient selected from a plurality of studies; (b) selecting as a ParameterA an anatomical characteristic in the primary Study and selecting as a ParameterB a Modality in the primary Study; (c) executing on a server digital data processor a render server program which applies one or more Study Selection Rules to: (i) generate a list of a plurality of secondary studies based on ParameterA and ParamaterB; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE.

In an embodiment, the method further includes the Study Selection Rule in step (c)(i)
 IF (Primary.Dicom.AnatomicalCharacteristic="ParameterA" and Primary.Dicom.Modality="ParameterB"),
THEN SELECT other studies for loading WHERE (Other.Dicom.AnatomicalCharacteristic="ParameterA" and Other.Dicom.Modality="ParameterB").

In an embodiment, the method further includes where in step (c)(ii) the CNN generates Primary.ImageContentBasedParameter="ParameterC" and Other.ImageContentBasedParameter="ParameterD", and the Study Selection Rule in step (c)(i) and in step (c)(iii)
 IF (Primary.Dicom.AnatomicalCharacteristic="ParameterA" and Primary.Dicom.Modality="ParameterB"),
THEN SELECT other studies for loading WHERE (Other.Dicom.AnatomicalCharacteristic="ParameterA" AND Other.Dicom.Modality="ParameterB" AND INTERSECTION(ParameterC,ParameterD) NOT EMPTY).

In an embodiment, the method further includes where a Study Selection Rule of the one or more Study Selection Rules in step (c)(i) requires
 IF (Primary.Dicom.AnatomicalCharacteristic="ParameterA" and Primary.Dicom.Modality="ParameterB"),
 THEN SELECT other studies for loading WHERE
(Other.Dicom.AnatomicalCharacteristic="ParameterA" AND Other.Dicom.Modality="ParameterB" AND INTERSECTION(Primary.ImageContentBasedParameter,Other.ImageContentBasedParameter) NOT EMPTY).

In an embodiment, the one or more ImageContentBased parameters are vertebrae. In an embodiment, the CNN identifies vertebrae in the primary Study selected from the group consisting of L1, L2, L3, L4, L5, C1, C2, C3, C4, C5, C6, C7, Th1, Th2, Th3, Th4, Th5, Th6, Th7, Th8, Th9, Th10, Th11, and Th12. In an embodiment, the CNN is pretrained with the plurality of studies. In an embodiment, the CNN is pretrained with a first plurality of studies where the first plurality of studies is selected based on the anatomical characteristic in the primary Study. In an embodiment, the CNN is pretrained with a first plurality of studies where the first plurality of studies is selected based on one or more ImageContentBased parameters identified in the primary Study.

In another aspect, there is provided a method including: (a) selecting a primary Study of a patient selected from a plurality of studies; (b) selecting as a ParameterA an anatomical characteristic in the primary Study; (c) executing on a server digital data processor a render server program which applies one or more Study Selection Rules to: (i) generate a list of a plurality of secondary studies based on ParameterA; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE.

In an embodiment, the method further includes where a Study Selection Rule of the one or more Study Selection Rules in step (c)(i) requires
 IF (Primary.Dicom.AnatomicalCharacteristic="ParameterA"),
THEN SELECT other studies for loading WHERE (Other.Dicom.AnatomicalCharacteristic="ParameterA").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) requires
 IF (Primary.Dicom.AnatomicalCharacteristic="ParameterA"),
THEN SELECT other studies for loading WHERE (Other.Dicom.AnatomicalCharacteristic="ParameterA" AND INTERSECTION(ParameterC,ParameterD) NOT EMPTY).

In an embodiment, the method further includes where a Study Selection Rule of the one or more Study Selection Rules requires
 IF (Primary.Dicom.AnatomicalCharacteristic="ParameterA"), THEN SELECT other studies for loading
WHERE
(Other.Dicom.AnatomicalCharacteristic="ParameterA"
AND INTERSECTION(Primary.ImageContentBasedParameter,Other.ImageContentBasedParameter) NOT EMPTY).

In an embodiment, the method further includes where a ParameterB is a Modality in the primary Study, where in step (c) the one or more Study Selection Rules restrict to studies where the Modality in the final list is equal to ParameterB.

In an embodiment, a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c)(i) requires
    IF (Primary.Dicom.AnatomicalCharacteristic="ParameterA" and Primary.Dicom.Modality="ParameterB"),
THEN SELECT other studies for loading WHERE (Other.Dicom.AnatomicalCharacteristic="ParameterA" and Other.Dicom.Modality="ParameterB").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
    IF (Primary.Dicom.AnatomicalCharacteristic="ParameterA" and Primary.Dicom.Modality="ParameterB"),
THEN SELECT other studies for loading WHERE (Other.Dicom.AnatomicalCharacteristic="ParameterA" AND Other.Dicom.Modality="ParameterB" AND INTERSECTION(ParameterC,ParameterD) NOT EMPTY).

In an embodiment, the method further includes wherein a Study Selection Rule of the one or more Study Selection Rules requires
    IF (Primary.Dicom.AnatomicalCharacteristic="ParameterA" and Primary.Dicom.Modality="ParameterB"),
    THEN SELECT other studies for loading
WHERE
(Other.Dicom.AnatomicalCharacteristic="ParameterA" AND Other.Dicom.Modality="ParameterB" AND INTERSECTION(Primary.ImageContentBasedParameter,Other.ImageContentBasedParameter) NOT EMPTY).

In another aspect, there is provided a method including: (a) selecting a primary Study of a patient selected from a plurality of studies; (b) selecting as a ParameterA a disease based characteristic in the primary Study; (c) executing on a server digital data processor a render server program which applies one or more Study Selection Rules to: (i) generate a list of a plurality of secondary studies based on ParameterA; (ii) generate from the list of the plurality of secondary studies one or more ImageContentBased parameters using Convolutional Neural Networks (CNN); (iii) select from the list of the plurality of secondary studies a final list based on the one or more ImageContentBased parameters;
(d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary Study and one or more of the plurality of secondary studies selected from the list based on the Display Protocol selected in step (d).

In an embodiment, the method further includes where a Study Selection Rule of the one or more Study Selection Rules in step (c)(i) requires
    IF (Primary.Dicom.DiseaseCharacteristic="ParameterA"),
    THEN SELECT other studies for loading WHERE (Other.Dicom.DiseaseCharacteristic="ParameterA").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
    IF (Primary.Dicom.DiseaseCharacteristic="ParameterA"),
    THEN SELECT other studies for loading WHERE (Other.Dicom.DiseaseCharacteristic="ParameterA" AND INTERSECTION(ParameterC,ParameterD) NOT EMPTY).

In an embodiment, the method further includes where a Study Selection Rule of the one or more Study Selection Rules requires
    IF (Primary.Dicom.AnatomicalCharacteristic="ParameterA"),
    THEN SELECT other studies for loading
WHERE
(Other.Dicom.AnatomicalCharacteristic="ParameterA" AND INTERSECTION(Primary.ImageContentBasedParameter,Other.ImageContentBasedParameter) NOT EMPTY).

In an embodiment, the method further includes where a ParameterB is a Modality in the primary Study, where in step (c) the one or more Study Selection Rules restrict to studies where the Modality in the final list is equal to ParameterB.

In an embodiment, a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c)(i) requires
    IF (Primary.Dicom.AnatomicalCharacteristic="ParameterA" and Primary.Dicom.Modality="ParameterB"),
    THEN SELECT other studies for loading WHERE (Other.Dicom.AnatomicalCharacteristic="ParameterA" and Other.Dicom.Modality "ParameterB").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require IF (Primary.Dicom.AnatomicalCharacteristic="ParameterA" and Primary.Dicom.Modality="ParameterB"),
THEN SELECT other studies for loading WHERE (Other.Dicom.AnatomicalCharacteristic="ParameterA" AND Other.Dicom.Modality "ParameterB" AND INTERSECTION(ParameterC,ParameterD) NOT EMPTY).

In an embodiment, the method further includes the Study Selection Rule
IF (Primary.Dicom.AnatomicalCharacteristic="ParameterA" and Primary.Dicom.Modality="ParameterB"),
THEN SELECT other studies for loading
WHERE (Other.Dicom.AnatomicalCharacteristic="ParameterA" AND Other.Dicom.Modality="ParameterB" AND INTERSECTION(Primary.ImageContentBasedParameter,Other.ImageContentBasedParameter) NOT EMPTY).

In another aspect, there is provided a method including: (a) selecting a primary Study of a patient selected from a plurality of studies; (b) selecting as a ParameterB a Modality in the primary Study and selecting as a ParameterA from the group consisting of an anatomical characteristic and a disease based characteristic in the primary Study; (c) executing on a server digital data processor a render server program which applies one or more Study Selection Rules to: (i) generate a list of a plurality of secondary studies based on ParameterA and ParamaterB; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary study and one or more of the plurality of secondary studies selected from the list based on the Display Protocol selected in step (d).

In an embodiment, the one or more ImageContentBased parameters are vertebrae. In an embodiment, the CNN identifies vertebrae in the primary study selected from the group consisting of L1, L2, L3, L4, L5, C1, C2, C3, C4, C5, C6, C7, Th1, Th2, Th3, Th4, Th5, Th6, Th7, Th8, Th9, Th10, Th11, and Th12. In an embodiment, the CNN is pretrained with the plurality of studies. In an embodiment, the CNN is pretrained with a first plurality of studies where the first plurality of studies is selected based on the anatomical characteristic in the primary study. In an embodiment, the CNN is pretrained with a first plurality of studies where the first plurality of studies is selected based on one or more ImageContentBased parameters identified in the primary study. In an embodiment, the one or more ImageContentBased parameters are vertebrae. In an embodiment, the CNN identifies vertebrae in the primary study selected from the group consisting of L1, L2, L3, L4, L5, C1, C2, C3, C4, C5, C6, C7, Th1, Th2, Th3, Th4, Th5, Th6, Th7, Th8, Th9, Th10, Th11, and Th12. In an embodiment, the CNN is pretrained with the plurality of studies where the first plurality of studies is selected based on the anatomical characteristic in the primary study. In an embodiment, the CNN is pretrained with a first plurality of studies where the first plurality of studies is selected based on the anatomical characteristic in the primary study. In an embodiment, the CNN is pretrained with a first plurality of studies where the first plurality of studies is selected based on one or more ImageContentBased parameters identified in the primary study.

In another aspect, there is provided a method including: (a) selecting a primary Study of a patient selected from a plurality of studies; (b) selecting as a ParameterA an AnatomicalCharacteristic in the primary study; (c) executing on a server digital data processor a render server program which applies one or more Study Selection Rules to generate a list of a plurality of secondary studies based on the ParameterA and one or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies, where the one or more Study Selection Rules restrict the plurality of secondary studies to studies of the patient selected from the plurality of studies, where the one or more Study Selection Rules restrict the plurality of secondary studies to studies of the AnatomicalCharacteristic in the primary study; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (e) displaying two or more of the plurality of secondary studies selected from the list based on the Display Protocol selected in step (d).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the one or more parameters include a ParameterB a Modality in the primary study and a ParameterY a Modality in a secondary study, where in step (c) the one or more Study Selection Rules restrict to studies where ParameterB is equal to ParameterY.

In an embodiment, the ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA). In an embodiment, when the ParameterB is Computed Radiography (CR) then the Modality in the two or more of the plurality of secondary studies is selected from the group consisting of Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c) requires
 IF (Primary.Dicom.AnatomicalCharacteristic= "ParameterA" and Primary.Dicom.Modality="CR"),
 THEN SELECT other secondary studies for loading WHERE (Other.Dicom.AnatomicalCharacteristic="ParameterA" and (Other.Dicom.Modality "CR") or Other.Dicom.Modality="CT").

In an embodiment, the method further includes where a Study Selection Rule of the one or more Study Selection Rules in step (c) requires
 IF (Primary.Dicom.AnatomicalCharacteristic= "ParameterA" and Primary.Dicom.Modality="ParameterB"),
 THEN SELECT other secondary studies for loading WHERE (Other.Dicom.AnatomicalCharacteristic="ParameterA" and (Other.Dicom.Modality="ParameterZ") AND INTERSECTION (ParameterB, ParameterZ) NOT EMPTY).

In an embodiment, the method further includes where a Study Selection Rule of the one or more Study Selection Rules in step (c) requires
 IF (Primary.Dicom.AnatomicalCharacteristic= "ParameterA" and Primary.Dicom.Modality="ParameterB"),
 THEN SELECT other secondary studies for loading WHERE (Other.Dicom.AnatomicalCharacteristic="ParameterA" and (Other.Dicom.Modality "ParameterY") AND INTERSECTION (ParameterB, ParameterY) EMPTY).

In an embodiment, the method further includes where a Study Selection Rule of the one or more Study Selection Rules in step (c) requires
 IF (Primary.Dicom.AnatomicalCharacteristic= "ParameterA" and Primary.Dicom.Modality="ParameterB")
 THEN SELECT other secondary studies for loading WHERE (Other.Dicom.AnatomicalCharacteristic="ParameterA" and (Other.Dicom.Modality "ParameterB" AND INTERSECTION(Primary.Dicom.AnatomicalFeature,Other.Dicom.AnatomicalFeature) NOT EMPTY).

In an embodiment, the method further includes where a Study Selection Rule of the one or more Study Selection Rules in step (c) requires
 IF (Primary.Dicom.AnatomicalCharacteristic="ParameterA" and Primary.Dicom.Modality="ParameterB")
 THEN SELECT other secondary studies for loading WHERE (Other.Dicom.AnatomicalCharacteristic="ParameterA" and (Other.Dicom.Modality NOT "ParameterB" AND INTERSECTION(Primary.Dicom.AnatomicalFeature,Other.Dicom.AnatomicalFeature) NOT EMPTY).

In an embodiment, the AnatomicalFeature is a medical condition. In an embodiment, the medical condition is selected from the group consisting of a fracture and a bleeding. In an embodiment, the AnatomicalFeature is a notation stored as meta data. In an embodiment, the AnatomicalFeature includes whether an organ is present in a study. In an embodiment, the ParameterA is selected from meta data stored in the primary Study.

In another aspect, there is provided a method including: (a) selecting a primary Study of a patient selected from a plurality of studies; (b) selecting as a ParameterA a disease based characteristic in the primary study; (c) executing on a server digital data processor a render server program which applies one or more Study Selection Rules to generate a list of a plurality of secondary studies based on the ParameterA and one or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies, where the one or more Study Selection Rules restrict the plurality of secondary studies to studies of the patient selected from the plurality of studies, where the one or more Study Selection Rules restrict the plurality of secondary studies to studies of the disease based characteristic in the primary study; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (e) displaying two or more of the plurality of secondary studies selected from the list based on the Display Protocol selected in step (d).

In an embodiment, the one or more parameters include a ParameterB a Modality in the primary study and a ParameterY a Modality in a secondary study, where in step (c) the one or more Study Selection Rules restrict to studies where ParameterB is equal to ParameterY.

In an embodiment, the method further includes where a Study Selection Rule of the one or more Study Selection Rules in step (c) requires
 SELECT other secondary studies for loading
 WHERE (Primary.Dicom.Modality="ParameterB" and (Other.Dicom.Modality="ParameterY" AND INTERSECTION(ParameterB,ParameterY) NOT EMPTY).

In an embodiment, the ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c) requires
 IF (Primary.Dicom.DiseaseCharacteristic="ParameterA" and Primary.Dicom.Modality="CR"),
 THEN SELECT other secondary studies for loading WHERE (Other.Dicom.DiseaseCharacteristic="ParameterA" and (Other.Dicom.Modality "CR" or Other.Dicom.Modality="CT")).

In an embodiment, the method further includes where a Study Selection Rule of the one or more Study Selection Rules in step (c) requires IF (Primary.Dicom.DiseaseCharacteristic="ParameterA"
   and Primary.Dicom.Modality="ParameterB"),
THEN SELECT other secondary studies for loading
WHERE
(Other.Dicom.DiseaseCharacteristic="ParameterA" and
(Other.Dicom.Modality "ParameterB" or
Other.Dicom.Modality="ParameterZ")).

In an embodiment, the method further includes where a Study Selection Rule of the one or more Study Selection Rules in step (c) requires
   IF (Primary.Dicom.DiseaseCharacteristic="ParameterA"
      and Primary.Dicom.Modality="ParameterB"),
   THEN SELECT other secondary studies for loading
WHERE
(Other.Dicom.DiseaseCharacteristic="ParameterA" and
(Other.Dicom.Modality "ParameterY")
WHERE Intersection (ParameterB, ParameterY) NOT EMPTY).

In an embodiment, the method further includes where a Study Selection Rule of the one or more Study Selection Rules in step (c) requires
   IF (Primary.Dicom.DiseaseCharacteristic="DISEASE 1"
      and Primary.Dicom.Modality="IMAGE TYPE 1"),
   THEN SELECT other secondary studies for loading
WHERE (Other.Dicom.DiseaseCharacteristic="DISEASE 1" and Other.Dicom.Modality "IMAGE TYPE 2").

In an embodiment, the method further includes where a Study Selection Rule of the one or more Study Selection Rules in step (c) requires
   IF (Primary.Dicom.DiseaseCharacteristic="Spinal Degradation" and
      Primary.Dicom.Modality="ParameterB")
   THEN SELECT other secondary studies for loading
WHERE (Other.Dicom.AnatomicalCharacteristic="Spinal Degradation" and Other.Dicom.Modality="ParameterB" AND INTERSECTION(Primary.Dicom.AnatomicalFeature,Other.Dicom.AnatomicalFeature) NOT EMPTY).

In an embodiment, the method further includes where a Study Selection Rule of the one or more Study Selection Rules in step (c) requires
   IF (Primary.Dicom.DiseaseCharacteristic="ParameterA"
      and Primary.Dicom.Modality="ParameterB")
   THEN SELECT other secondary studies for loading
WHERE
(Other.Dicom.DiseaseCharacteristic="ParameterA" and Other.Dicom.Modality "ParameterB" AND INTERSECTION(Primary.Dicom.AnatomicalFeature,Other.Dicom.AnatomicalFeature) NOT EMPTY).

In an embodiment, the AnatomicalFeature is a medical condition. In an embodiment, the medical condition is selected from the group consisting of a fracture and a bleeding. In an embodiment, the AnatomicalFeature is a notation stored as meta data. In an embodiment, the AnatomicalFeature includes whether an organ is present in a study. In an embodiment, the ParameterA is selected from meta data stored in the primary Study.

In another aspect, there is provided a method including: (a) selecting a primary Study of a patient selected from a plurality of studies; (b) selecting a ParameterA from the primary study, where the ParameterA is selected from the group consisting of an anatomical characteristic, an anatomical region imaged, and a disease based characteristic; (c) executing on a server digital data processor a render server program which applies one or more Study Selection Rules to generate a list of a plurality of secondary studies based on the ParameterA and one or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies, where the one or more Study Selection Rules restrict the plurality of secondary studies to studies of the patient selected from the plurality of studies, where the one or more Study Selection Rules restrict the plurality of secondary studies to studies of the ParameterA selected;
(d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (e) displaying two or more of the plurality of secondary studies selected from the list based on the Display Protocol selected in step (d).

In an embodiment, ParameterA is the anatomical region imaged selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the one or more parameters include a ParameterB a Modality in the primary study and a ParameterY a Modality in a secondary study, where in step (c) the one or more Study Selection Rules restrict to studies where ParameterB is equal to ParameterY.

In an embodiment, the method further includes where a Study Selection Rule of the one or more Study Selection Rules in step (c) requires
   SELECT other secondary studies for loading
   WHERE (Primary.Dicom.Modality="ParameterB" and (Other.Dicom.Modality="ParameterY" AND INTERSECTION(ParameterB,ParameterY) NOT EMPTY).

In an embodiment, the ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c) requires
   IF (Primary.Dicom.AnatomicalCharacteristic=
      "ParameterA" and Primary.Dicom.Modality="CR"),
   THEN SELECT other secondary studies for loading
WHERE
(Other.Dicom.AnatomicalCharacteristic="ParameterA" and Other.Dicom.Modality "CR" or (Other.Dicom.Modality="CT")).

In an embodiment, the method further includes where a Study Selection Rule of the one or more Study Selection Rules in step (c) requires
   IF (Primary.Dicom.AnatomicalCharacteristic=
      "ParameterA" and
      Primary.Dicom.Modality="ParameterB"),
   THEN SELECT other secondary studies for loading
WHERE
(Other.Dicom.AnatomicalCharacteristic="ParameterA" and (Other.Dicom.Modality "ParameterB" or Other.Dicom.Modality="ParameterZ") WHERE Intersection (ParameterB, ParameterZ) EMPTY).

In an embodiment, the method further includes where a Study Selection Rule of the one or more Study Selection Rules in step (c) requires IF (Primary.Dicom.AnatomicalCharacteristic= "ParameterA" and Primary.Dicom.Modality="ParameterB"), THEN SELECT other secondary studies for loading WHERE (Other.Dicom.AnatomicalCharacteristic="ParameterA" and (Other.Dicom.Modality "ParameterY") AND INTERSECTION (ParameterB, ParameterY) NOT EMPTY).

In an embodiment, the method further includes where a Study Selection Rule of the one or more Study Selection Rules in step (c) requires IF (Primary.Dicom.AnatomicalCharacteristic="Spine" and Primary.Dicom.Modality="ParameterB")

THEN SELECT other secondary studies for loading WHERE (Other.Dicom.AnatomicalCharacteristic="Spine" and Other.Dicom.Modality "ParameterB" AND INTERSECTION(Primary.Dicom.AnatomicalFeature,Other.Dicom.AnatomicalFeature) NOT EMPTY).

In an embodiment, the method further includes where a Study Selection Rule of the one or more Study Selection Rules in step (c) requires IF (Primary.Dicom.AnatomicalCharacteristic= "ParameterA" and Primary.Dicom.Modality="ParameterB")

THEN SELECT other secondary studies for loading WHERE (Other.Dicom.AnatomicalCharacteristic="ParameterA" and Other.Dicom.Modality "ParameterB" AND INTERSECTION(Primary.Dicom.AnatomicalFeature,Other.Dicom.AnatomicalFeature) NOT EMPTY).

In an embodiment, the AnatomicalFeature is a medical condition. In an embodiment, the medical condition is selected from the group consisting of a fracture and a bleeding. In an embodiment, the AnatomicalFeature is a notation stored as meta data. In an embodiment, the AnatomicalFeature includes whether an organ is present in a study. In an embodiment, the ParameterA is selected from meta data stored in the primary Study.

In an embodiment, the method further includes where a Study Selection Rule of the one or more Study Selection Rules in step (c) requires IF (Primary.Dicom.DiseaseCharacteristic="ParameterA" and Primary.Dicom.Modality="CR"), THEN SELECT other secondary studies for loading WHERE (Other.Dicom.DiseaseCharacteristic="ParameterA" and Other.Dicom.Modality "CR" or Other.Dicom.Modality="CT").

In an embodiment, the method further includes where a Study Selection Rule of the one or more Study Selection Rules in step (c) requires IF (Primary.Dicom.DiseaseCharacteristic="ParameterA" and Primary.Dicom.Modality="ParameterB"), THEN SELECT other secondary studies for loading WHERE (Other.Dicom.DiseaseCharacteristic="ParameterA" and (Other.Dicom.Modality "ParameterB" or Other.Dicom.Modality="ParameterZ") WHERE Intersection (ParameterB, ParameterZ) EMPTY).

In an embodiment, the method further includes where a Study Selection Rule of the one or more Study Selection Rules in step (c) requires IF (Primary.Dicom.DiseaseCharacteristic="ParameterA" and Primary.Dicom.Modality="ParameterB"), THEN SELECT other secondary studies for loading WHERE (Other.Dicom.DiseaseCharacteristic="ParameterA" and Other.Dicom.Modality "ParameterY" WHERE Intersection (ParameterB, ParameterY) NOT EMPTY).

In an embodiment, the method further includes where a Study Selection Rule of the one or more Study Selection Rules in step (c) requires IF (Primary.Dicom.DiseaseCharacteristic="ParameterA" and Primary.Dicom.Modality="ParameterB"), THEN SELECT other secondary studies for loading WHERE (Other.Dicom.DiseaseCharacteristic="ParameterA" and Other.Dicom.Modality "ParameterB").

In an embodiment, the method further includes where a Study Selection Rule of the one or more Study Selection Rules in step (c) requires IF (Primary.Dicom.DiseaseCharacteristic="Spinal Degradation" and Primary.Dicom.Modality="ParameterB")

THEN SELECT other secondary studies for loading WHERE (Other.Dicom.AnatomicalCharacteristic="Spinal Degradation" and Other.Dicom.Modality="ParameterB" AND INTERSECTION(Primary.Dicom.AnatomicalFeature,Other.Dicom.AnatomicalFeature) NOT EMPTY).

In an embodiment, the AnatomicalFeature is a medical condition.

In another aspect, there is provided a method including: (a) selecting a primary Study of a patient selected from a plurality of studies; (b) selecting a ParameterA from the primary study, where the ParameterA is selected from the group consisting of an anatomical characteristic; (c) selecting ParameterB selected from the group consisting of one or more of regions of the anatomical characteristic, parts of a skeletal system of the anatomical characteristic, and organs of the anatomical characteristic; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the anatomical characteristic is selected from the group consisting of HEAD, EYE, EAR, NOSE, NOSTRIL, MOUTH, LIP, PHILTRUM, JAW, MANDIBLE, GINGIVA, TOOTH, TONGUE, THROAT, LARYNGEAL PROMINENCE, VERTEBRAL COLUMN, SCAPULA, HUMERUS, ELBOW, RADIUS, ULNA, CARPUS, METACARPUS, PHALANGES, THUMB, NAILS, THORAX, BREAST, ABDOMEN, PENIS, SCROTUM, VULVA, LEG, FEMUR, KNEE, PATELLA, TIBIA, SURA, TALOCRURAL REGION, METATARSUS, PHALANGES PROXIMALES, PHALANGES MEDIAE, AND PHALANGES DISTALES.

In an embodiment, the method further includes where a Study Selection Rule of the one or more Study Selection Rules in step (d) requires IF (Primary.Dicom.AnatomicalCharacteristic= "ParameterA" and Primary.Dicom.RegionAnatomicalCharacteristic= "ParameterB"), THEN SELECT other secondary studies for loading WHERE (Other.Dicom.AnatomicalCharacteristic="ParameterA" and Other.Dicom.OrganAnatomicalCharacteristic="ParameterC").

In an embodiment, one or both the ParameterA and the ParameterB are selected from meta data stored in the primary Study.

In another aspect, there is provided a method including: (a) selecting a primary Study of a patient selected from a plurality of studies, where the primary Study is an image measured after the patient has a contrast agent administered; (b) selecting a ParameterA an AnatomicalCharacteristic from the primary study; (c) selecting ParameterB a Modality from the primary study; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient before the contrast agent was administered selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (d) requires IF (Primary.Dicom.AnatomicalCharacteristic= "ParameterA" and Primary.Dicom.Modality="CR"), THEN SELECT other secondary studies for loading WHERE (Other.Dicom.AnatomicalCharacteristic="ParameterA" and Other.Dicom.Modality "CR" or Other.Dicom.Modality="CT").

In an embodiment, one or both the ParameterA and the ParameterB are selected from meta data stored in the primary Study.

In another aspect, there is provided a method including: (a) selecting a primary Study of a patient selected from a plurality of studies; (b) selecting a ParameterA an AnatomicalCharacteristic from the primary study; (c) selecting ParameterB selected from the group consisting of one or more anatomical characteristics of the AnatomicalCharacteristic, parts of a skeletal system of the AnatomicalCharacteristic, organs of the AnatomicalCharacteristic and Modality of the primary Study; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (d) requires IF (Primary.Dicom.AnatomicalCharacteristic="SPINE" and Primary.Dicom.AnatomicalFeature="ParameterB")

THEN SELECT other secondary studies for loading WHERE (Other.Dicom.AnatomicalCharacteristic="SPINE" and Other.Dicom.AnatomicalFeature="ParameterB" AND INTERSECTION(Primary.AnatomicalFeature,Other.AnatomicalFeature) NOT EMPTY).

In an embodiment, the ParameterA is selected from meta data stored in the primary Study.

In another aspect, there is provided a including: (a) selecting a primary Study of a patient selected from a plurality of studies; (b) selecting a ParameterA from the primary study, where the ParameterA is selected from the group consisting of an anatomical characteristic, and a disease based characteristic; (c) selecting ParameterB from the group consisting of one or more anatomical features of the ParameterA, parts of a skeletal system of the ParameterA, organs of the ParameterA, and a Modality of the primary Study; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the anatomical characteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the ParameterB is a Modality in the primary study and a ParameterY a Modality in a secondary study, where in step (d) the one or more Study Selection Rules restrict to studies where ParameterB is equal to ParameterY.

In an embodiment, the method further includes where a Study Selection Rule of the one or more Study Selection Rules in step (d) requires SELECT other secondary studies for loading
WHERE (Primary.Dicom.Modality="ParameterB" and (Other.Dicom.Modality="ParameterY" AND INTERSECTION(ParameterB,ParameterY) NOT EMPTY).

In an embodiment, the ParameterB is a Modality selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (d) requires IF    (Primary.Dicom.AnatomicalCharacteristic="ParameterA" and Primary.Dicom.Modality="ParameterB"), THEN SELECT other secondary studies for loading
WHERE (Other.Dicom.AnatomicalCharacteristic="ParameterA" and Other.Dicom.Modality "ParameterB").

In an embodiment, the method further includes where a Study Selection Rule of the one or more Study Selection Rules in step (d) requires IF    (Primary.Dicom.AnatomicalCharacteristic="ParameterA" and Primary.Dicom.Modality="ParameterB"), THEN SELECT other secondary studies for loading
WHERE (Other.Dicom.AnatomicalCharacteristic="ParameterA" and Other.Dicom.Modality "ParameterY" AND INTERSECTION (ParameterB, ParameterY) NOT EMPTY).

In an embodiment, the method further includes where a Study Selection Rule of the one or more Study Selection Rules in step (d) requires IF    (Primary.Dicom.AnatomicalCharacteristic="ParameterA" and Primary.Dicom.Modality="ParameterB")

THEN SELECT other secondary studies for loading
WHERE (Other.Dicom.AnatomicalCharacteristic="ParameterA" and (Other.Dicom.Modality "ParameterB" AND INTERSECTION(Primary.Dicom.AnatomicalFeature,Other.Dicom.AnatomicalFeature) NOT EMPTY).

In an embodiment, the method further includes where a Study Selection Rule of the one or more Study Selection Rules in step (d) requires IF    (Primary.Dicom.AnatomicalCharacteristic="ParameterA")

THEN SELECT other secondary studies for loading
WHERE (Other.Dicom.AnatomicalCharacteristic="ParameterA" AND INTERSECTION(Primary.Dicom.AnatomicalFeature,Other.Dicom.AnatomicalFeature) NOT EMPTY).

In another aspect, there is provided a method including: (a) selecting a primary Study of a patient selected from a plurality of studies; (b) selecting as a ParameterA an anatomical characteristic imaged; (c) selecting ParameterB from the group consisting of one or more anatomical features of the ParameterA, parts of a skeletal system of the ParameterA, organs of the ParameterA, and a Modality of the primary Study; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the anatomical characteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE. In an embodiment, the ParameterB is a Modality in the primary study and a ParameterY a Modality in a secondary study, where in step (d) the one or more Study Selection Rules restrict to studies where ParameterB is equal to ParameterY.

In an embodiment, the method further includes where a Study Selection Rule of the one or more Study Selection Rules in step (d) requires SELECT other secondary studies for loading
WHERE (Primary.Dicom.Modality="ParameterB" and (Other.Dicom.Modality="ParameterY" AND INTERSECTION(ParameterB,ParameterY) NOT EMPTY).

In an embodiment, the ParameterB is a Modality selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (d) requires
IF (Primary.Dicom.AnatomicalCharacteristic= "ParameterA" and
Primary.Dicom.Modality="ParameterB"),
THEN SELECT other secondary studies for loading
WHERE
(Other.Dicom.AnatomicalCharacteristic="ParameterA" and Other.Dicom.Modality "ParameterB").

In an embodiment, the method further includes the Study Selection Rule
IF
(Primary.Dicom.AnatomicalCharacteristic="ParameterA" and Primary.Dicom.Modality="ParameterB"),
THEN SELECT other secondary studies for loading
WHERE
(Other.Dicom.AnatomicalCharacteristic="ParameterA" and Other.Dicom.Modality "ParameterY" AND INTERSECTION (ParameterB, ParameterY) NOT EMPTY).

In an embodiment, the method further includes where a Study Selection Rule of the one or more Study Selection Rules in step (d) requires
IF
(Primary.Dicom.AnatomicalCharacteristic="ParameterA" and Primary.Dicom.Modality="ParameterB")
THEN SELECT other secondary studies for loading
WHERE
(Other.Dicom.AnatomicalCharacteristic="ParameterA" and (Other.Dicom.Modality "ParameterB" AND INTERSECTION(Primary.Dicom.AnatomicalFeature,Other.Dicom.AnatomicalFeature) NOT EMPTY).

In an embodiment, the method further includes where a Study Selection Rule of the one or more Study Selection Rules in step (d) requires
IF
(Primary.Dicom.AnatomicalCharacteristic="ParameterA")
THEN SELECT other secondary studies for loading
WHERE
(Other.Dicom.AnatomicalCharacteristic="ParameterA"
AND INTERSECTION(Primary.Dicom.AnatomicalFeature,Other.Dicom.AnatomicalFeature) NOT EMPTY).

In another aspect, there is provided a method including:
(a) selecting a primary Study of a patient selected from a plurality of studies; (b) selecting as a ParameterA a disease based characteristic; (c) selecting ParameterB from the group consisting of one or more anatomical features of the ParameterA, parts of a skeletal system of the ParameterA, organs of the ParameterA, and a Modality of the primary Study; (d) executing on a server digital data processor a render server program which applies one or more Study Selection Rules to generate a list of a plurality of secondary studies based on the ParameterA and the ParameterB, where the one or more Study Selection Rules restrict the plurality of secondary studies to studies of the patient selected from the plurality of studies; (e) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies and one or more Abstract Tags from the plurality of secondary studies; and (f) displaying two or more of the plurality of secondary studies selected from the list based on the Display Protocol selected in step (e).

In an embodiment, the method further includes where a Study Selection Rule of the one or more Study Selection Rules in step (d) requires
IF (Primary.Dicom.AnatomicalCharacteristic= "ParameterA")
THEN SELECT other secondary studies for loading
WHERE
(Other.Dicom.AnatomicalCharacteristic="ParameterA"
AND INTERSECTION(Primary.Dicom.AnatomicalFeature,Other.Dicom.AnatomicalFeature) NOT EMPTY).

In another aspect, there is provided a method including:
(a) selecting a primary Study of a patient selected from a plurality of studies; (b) selecting as a ParameterA an anatomical characteristic in the primary study; (c) executing on a server digital data processor a render server program which applies one or more Study Selection Rules to: (i) generate a list of a plurality of secondary studies based on ParameterA; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary study and one or more of the plurality of secondary studies selected from the list based on the Display Protocol selected in step (d).

In an embodiment, the AnatomicalCharacteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE.

In an embodiment, the method further includes where a Study Selection Rule of the one or more Study Selection Rules in step (c)(i) requires
IF (Primary.Dicom.AnatomicalCharacteristic= "ParameterA"),
THEN SELECT other studies for loading WHERE (Other.Dicom.AnatomicalCharacteristic="ParameterA").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require IF (Primary.Dicom.AnatomicalCharacteristic= "ParameterA"),
THEN SELECT other studies for loading WHERE (Other.Dicom.AnatomicalCharacteristic="ParameterA" AND INTERSECTION(ParameterC,ParameterD) NOT EMPTY).

In an embodiment, the method further includes where a Study Selection Rule of the one or more Study Selection Rules requires
IF (Primary.Dicom.AnatomicalCharacteristic= "ParameterA"),
THEN SELECT other studies for loading
WHERE
(Other.Dicom.AnatomicalCharacteristic="ParameterA" AND INTERSECTION(Primary.ImageContentBasedParameter,Other.ImageContentBasedParameter) NOT EMPTY).

In an embodiment, the method further includes where a ParameterB is a Modality in the primary study, where in step (c) the one or more Study Selection Rules restrict to studies where the Modality in the final list is equal to ParameterB.

In an embodiment, a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c)(i) requires
IF (Primary.Dicom.AnatomicalCharacteristic= "ParameterA" and Primary.Dicom.Modality="ParameterB"),
THEN SELECT other studies for loading WHERE (Other.Dicom.AnatomicalCharacteristic="ParameterA" and Other.Dicom.Modality="ParameterB").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
IF (Primary.Dicom.AnatomicalCharacteristic= "ParameterA" and Primary.Dicom.Modality="ParameterB"),
THEN SELECT other studies for loading WHERE (Other.Dicom.AnatomicalCharacteristic="ParameterA" AND Other.Dicom.Modality="ParameterB" AND INTERSECTION(ParameterC,ParameterD) NOT EMPTY).

In an embodiment, the method further includes where a Study Selection Rule of the one or more Study Selection Rules in step (c)(i) and in step (c)(iii) requires
IF (Primary.Dicom.AnatomicalCharacteristic= "ParameterA" and Primary.Dicom.Modality="ParameterB"),
THEN SELECT other studies for loading
WHERE
(Other.Dicom.AnatomicalCharacteristic="ParameterA" AND Other.Dicom.Modality="ParameterB" AND INTERSECTION(Primary.ImageContentBasedParameter,Other.ImageContentBasedParameter) NOT EMPTY).

In an embodiment, the one or more ImageContentBased parameters are vertebrae. In an embodiment, the CNN identifies vertebrae in the primary study selected from the group consisting of L1, L2, L3, L4, L5, C1, C2, C3, C4, C5, C6, C7, Th1, Th2, Th3, Th4, Th5, Th6, Th7, Th8, Th9, Th10, Th11, and Th12. In an embodiment, the CNN is pretrained with the plurality of studies. In an embodiment, the CNN is pretrained with a first plurality of studies where the first plurality of studies is selected based on the anatomical characteristic in the primary study. In an embodiment, the CNN is pretrained with a first plurality of studies where the first plurality of studies is selected based on one or more ImageContentBased parameters identified in the primary study.

In another aspect, there is provided a method including: (a) selecting a primary Study of a patient selected from a plurality of studies; (b) selecting as a ParameterA a disease based characteristic in the primary study; (c) executing on a server digital data processor a render server program which applies one or more Study Selection Rules to: (i) generate a list of a plurality of secondary studies based on ParameterA; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary study and one or more of the plurality of secondary studies selected from the list based on the Display Protocol selected in step (d).

In an embodiment, the method further including where a Study Selection Rule of the one or more Study Selection Rules in step (c)(i) requires
IF
(Primary.Dicom.DiseaseCharacteristic="ParameterA"),
THEN SELECT other studies for loading WHERE (Other.Dicom.DiseaseCharacteristic="ParameterA").

In an embodiment, the method further includes where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
IF
(Primary.Dicom.DiseaseCharacteristic="ParameterA"),
THEN SELECT other studies for loading WHERE (Other.Dicom.DiseaseCharacteristic="ParameterA" AND INTERSECTION(ParameterC,ParameterD) NOT EMPTY).

In an embodiment, the method further includes where a Study Selection Rule of the one or more Study Selection Rules in step (c)(i) requires
IF (Primary.Dicom.AnatomicalCharacteristic= "ParameterA"),
THEN SELECT other studies for loading
WHERE
(Other.Dicom.AnatomicalCharacteristic="ParameterA" AND INTERSECTION(Primary.ImageContentBasedParameter,Other.ImageContentBasedParameter) NOT EMPTY).

In an embodiment, the method further includes where a ParameterB is a Modality in the primary study, where in step (c) the one or more Study Selection Rules restrict to studies where the Modality in the final list is equal to ParameterB.

In an embodiment, a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

In an embodiment, the method further includes where a Study Selection Rule of the one or more Study Selection Rules in step (c)(i) require IF (Primary.Dicom.AnatomicalCharacteristic= "ParameterA" and Primary.Dicom.Modality="ParameterB"),
THEN SELECT other studies for loading WHERE (Other.Dicom.AnatomicalCharacteristic="ParameterA" and Other.Dicom.Modality "ParameterB").

In an embodiment, the method further including where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require IF (Primary.Dicom.AnatomicalCharacteristic= "ParameterA" and Primary.Dicom.Modality="ParameterB"),
THEN SELECT other studies for loading
WHERE
(Other.Dicom.AnatomicalCharacteristic="ParameterA"
AND Other.Dicom.Modality="ParameterB" AND INTERSECTION(ParameterC,ParameterD) NOT EMPTY).

In an embodiment, the method further includes where a Study Selection Rule of the one or more Study Selection Rules in step (c)(i) requires IF (Primary.Dicom.AnatomicalCharacteristic= "ParameterA" and Primary.Dicom.Modality="ParameterB"),
THEN SELECT other studies for loading
WHERE
(Other.Dicom.AnatomicalCharacteristic="ParameterA"
AND Other.Dicom.Modality="ParameterB" AND INTERSECTION(Primary.ImageContentBasedParameter,Other.ImageContentBasedParameter) NOT EMPTY).

In another aspect, there is provided a method including: (a) selecting a primary Study of a patient selected from a plurality of studies; (b) selecting as a ParameterB a Modality in the primary study and selecting as a ParameterA from the group consisting of an anatomical characteristic and a disease based characteristic in the primary study; (c) executing on a server digital data processor a render server program which applies one or more Study Selection Rules to: (i) generate a list of a plurality of secondary studies based on ParameterA and ParamaterB; (ii) generate from the list of the plurality of secondary studies one or more ImageContentBased parameters using Convolutional Neural Networks (CNN); (iii) select from the list of the plurality of secondary studies a final list based on the one or more ImageContentBased parameters; (d) executing on the server digital data processor the render server program which applies one or more Protocol Selection Rules to select a Display Protocol, where the one or more Protocol Selection Rules are based on two or more parameters selected from the group consisting of one or more DICOM parameters from the primary Study, one or more Abstract Tags from the primary Study, one or more DICOM parameters from the plurality of secondary studies, one or more Abstract Tags from the plurality of secondary studies and one or more ImageContentBased parameters; and (e) displaying the primary study and one or more of the plurality of secondary studies selected from the list based on the Display Protocol selected in step (d).

What is claimed is:

1. A method comprising:
(a) selecting a primary Study of a patient selected from a plurality of studies;
(b) selecting as a ParameterA an anatomical characteristic in the primary Study;
(c) executing on a server digital data processor a render server program which applies one or more Study Selection Rules to
(i) generate a list of a plurality of secondary studies based on ParameterA;
(ii) generate from the list of the plurality of secondary studies one or more ImageContentBased parameters using Convolutional Neural Networks (CNN);
(iii) select from the list of the plurality of secondary studies a final list based on the one or more ImageContentBased parameters;
(d) executing on the server digital data processor the render server program which applies one or more Protocol Selection Rules to select a Display Protocol, where the one or more Protocol Selection Rules are based on two or more parameters selected from the group consisting of one or more Digital Imaging and Communications in Medicine (DICOM) parameters from the primary Study, one or more Abstract Tags from the primary Study, one or more DICOM parameters from the plurality of secondary studies, one or more Abstract Tags from the plurality of secondary studies and one or more ImageContentBased parameters; and
(e) displaying the primary Study and one or more of the plurality of secondary studies selected from the list based on the Display Protocol selected in step (d).

2. The method of claim 1, where the anatomical characteristic is selected from the group consisting of SPINE, CHEST, ABDOMEN, BREAST, SHOULDER, TRAPEZIUS, ARM, ELBOW, WRIST, FINGER, PELVIS, HIP, FIBULAR, KNEE, TIBULAR, ANKLE, FOOT, NECK, HEAD, TEMPOROMANDIBULAR JUNCTION, FACE, BRAIN, DENTITION, SINUS, ADRENALS, RETINA, PITUITARY, and PROSTATE.

3. The method of claim 1, further comprising where a Study Selection Rule of the one or more Study Selection Rules in step (c)(i) requires IF (Primary.Dicom.AnatomicalCharacteristic= "ParameterA"),
THEN SELECT other studies for loading WHERE (Other.Dicom.AnatomicalCharacteristic= "ParameterA").

4. The method of claim 1, further comprising where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) requires IF (Primary.Dicom.AnatomicalCharacteristic= "ParameterA"),
THEN SELECT other studies for loading WHERE (Other.Dicom.AnatomicalCharacteristic="ParameterA" AND INTERSECTION(ParameterC,ParameterD) NOT EMPTY).

5. The method of claim 1, further comprising where a Study Selection Rule of the one or more Study Selection Rules requires IF (Primary.Dicom.AnatomicalCharacteristic= "ParameterA"),
THEN SELECT other studies for loading
WHERE (Other.Dicom.AnatomicalCharacteristic="ParameterA" AND INTERSECTION(Primary.ImageContentBasedParameter,Other.ImageContentBasedParameter) NOT EMPTY).

6. The method of claim 1, further comprising where a ParameterB is a Modality in the primary Study, where in step (c) the one or more Study Selection Rules restrict to studies where the Modality in the final list is equal to ParameterB.

7. The method of claim 6, where a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

8. The method of claim 6, further comprising where a Study Selection Rule of the one or more Study Selection Rules in step (c)(i) requires
IF (Primary.Dicom.AnatomicalCharacteristic= "ParameterA" and Primary.Dicom.Modality "ParameterB"),
THEN SELECT other studies for loading WHERE (Other.Dicom.AnatomicalCharacteristic="ParameterA" and Other.Dicom.Modality="ParameterB").

9. The method of claim 6, further comprising where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
IF (Primary.Dicom.AnatomicalCharacteristic= "ParameterA" and Primary.Dicom.Modality "ParameterB"),
THEN SELECT other studies for loading WHERE (Other.Dicom.AnatomicalCharacteristic= "ParameterA" AND Other.Dicom.Modality="ParameterB" AND INTERSECTION(ParameterC,ParameterD) NOT EMPTY).

10. The method of claim 6, further comprising wherein a Study Selection Rule of the one or more Study Selection Rules requires
IF (Primary.Dicom.AnatomicalCharacteristic= "ParameterA" and Primary.Dicom.Modality "ParameterB"),
THEN SELECT other studies for loading
WHERE (Other.Dicom.AnatomicalCharacteristic= "ParameterA" AND Other.Dicom.Modality="ParameterB" AND INTERSECTION(Primary.ImageContentBasedParameter, Other.ImageContentBasedParameter) NOT EMPTY).

11. A method comprising:
(a) selecting a primary Study of a patient selected from a plurality of studies;
(b) selecting as a ParameterA a disease based characteristic in the primary Study;
(c) executing on a server digital data processor a render server program which applies one or more Study Selection Rules to
(i) generate a list of a plurality of secondary studies based on ParameterA;
(ii) generate from the list of the plurality of secondary studies one or more ImageContentBased parameters using Convolutional Neural Networks (CNN);
(iii) select from the list of the plurality of secondary studies a final list based on the one or more ImageContentBased parameters;
(d) executing on the server digital data processor the render server program which applies one or more Protocol Selection Rules to select a Display Protocol, where the one or more Protocol Selection Rules are based on two or more parameters selected from the group consisting of one or more Digital Imaging and Communications in Medicine (DICOM) parameters from the primary Study, one or more Abstract Tags from the primary Study, one or more DICOM parameters from the plurality of secondary studies, one or more Abstract Tags from the plurality of secondary studies and one or more ImageContentBased parameters; and
(e) displaying the primary Study and one or more of the plurality of secondary studies selected from the list based on the Display Protocol selected in step (d).

12. The method of claim 11, further comprising where a Study Selection Rule of the one or more Study Selection Rules in step (c)(i) requires
IF (Primary.Dicom.DiseaseCharacteristic= "ParameterA"),
THEN SELECT other studies for loading WHERE (Other.Dicom.DiseaseCharacteristic="ParameterA").

13. The method of claim 11, further comprising where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require
IF (Primary.Dicom.DiseaseCharacteristic= "ParameterA"),
THEN SELECT other studies for loading WHERE (Other.Dicom.DiseaseCharacteristic="ParameterA" AND INTERSECTION(ParameterC,ParameterD) NOT EMPTY).

14. The method of claim 11, further comprising where a Study Selection Rule of the one or more Study Selection Rules requires
IF (Primary.Dicom.AnatomicalCharacteristic= "ParameterA"),
THEN SELECT other studies for loading
WHERE (Other.Dicom.AnatomicalCharacteristic= "ParameterA" AND INTERSECTION(Primary.ImageContentBasedParameter,Other.ImageContentBasedParameter) NOT EMPTY).

15. The method of claim 11, further comprising where a ParameterB is a Modality in the primary Study, where in step (c) the one or more Study Selection Rules restrict to studies where the Modality in the final list is equal to ParameterB.

16. The method of claim 15, where a ParameterB is selected from the group consisting of Computed Radiography (CR), Computer Tomography (CT), Digital Radiography (DX), Mammography (MG), Magnetic Resonance (MR), Opthalmic Photography (OP), Positron Emission Tomography (PT), Radio Fluoroscopy (RF), and X-Ray Angiography (XA).

17. The method of claim 15, further comprising where a Study Selection Rule of the one or more Study Selection Rules in step (c)(i) requires IF (Primary.Dicom.AnatomicalCharacteristic= "ParameterA" and Primary.Dicom.Modality "ParameterB"), THEN SELECT other studies for loading WHERE (Other.Dicom.AnatomicalCharacteristic= "ParameterA" and Other.Dicom.Modality="ParameterB").

18. The method of claim 15, further comprising where in step (c)(ii) the CNN generates Primary.ImageContentBasedParameter="ParameterC" and Other.ImageContentBasedParameter="ParameterD", and a Study Selection Rule of the one or more Study Selection Rules in step (c)(i) and in step (c)(iii) require IF (Primary.Dicom.AnatomicalCharacteristic= "ParameterA" and Primary.Dicom.Modality "ParameterB"), THEN SELECT other studies for loading WHERE (Other.Dicom.AnatomicalCharacteristic= "ParameterA" AND Other.Dicom.Modality="ParameterB" AND INTERSECTION(ParameterC,ParameterD) NOT EMPTY).

19. The method of claim 15, further comprising the Study Selection Rule

IF (Primary.Dicom.AnatomicalCharacteristic= "ParameterA" and Primary.Dicom.Modality "ParameterB"), THEN SELECT other studies for loading WHERE (Other.Dicom.AnatomicalCharacteristic="ParameterA" AND Other.Dicom.Modality="ParameterB" AND INTERSECTION(Primary.ImageContentBasedParameter,Other.ImageContentBasedParameter) NOT EMPTY).

20. A method comprising:
(a) selecting a primary Study of a patient selected from a plurality of studies;
(b) selecting as a ParameterB a Modality in the primary Study and selecting as a ParameterA from the group consisting of an anatomical characteristic and a disease based characteristic in the primary Study;
(c) executing on a server digital data processor a render server program which applies one or more Study Selection Rules to
    (i) generate a list of a plurality of secondary studies based on ParameterA and ParamaterB;
    (ii) generate from the list of the plurality of secondary studies one or more ImageContentBased parameters using Convolutional Neural Networks (CNN);
    (iii) select from the list of the plurality of secondary studies a final list based on the one or more ImageContentBased parameters;
(d) executing on the server digital data processor the render server program which applies one or more Protocol Selection Rules to select a Display Protocol, where the one or more Protocol Selection Rules are based on two or more parameters selected from the group consisting of one or more Digital Imaging and Communications in Medicine (DICOM) parameters from the primary Study, one or more Abstract Tags from the primary Study, one or more DICOM parameters from the plurality of secondary studies, one or more Abstract Tags from the plurality of secondary studies and one or more ImageContentBased parameters; and
(e) displaying the primary Study and one or more of the plurality of secondary studies selected from the list based on the Display Protocol selected in step (d).

* * * * *